(12) United States Patent
De Brouwer et al.

(10) Patent No.: US 11,853,891 B2
(45) Date of Patent: Dec. 26, 2023

(54) SYSTEM AND METHOD WITH FEDERATED LEARNING MODEL FOR MEDICAL RESEARCH APPLICATIONS

(71) Applicant: SHARECARE AI, INC., Palo Alto, CA (US)

(72) Inventors: Walter Adolf De Brouwer, Los Altos, CA (US); Srivatsa Akshay Sharma, Palo Alto, CA (US); Neerajshyam Rangan Kashyap, Palo Alto, CA (US); Kartik Thakore, Palo Alto, CA (US); Philip Joseph Dow, South Lake Tahoe, CA (US)

(73) Assignee: SHARECARE AI, INC., Palo Alto, CA (US)

( * ) Notice: Subject to any disclaimer, the term of this patent is extended or adjusted under 35 U.S.C. 154(b) by 589 days.

(21) Appl. No.: 16/816,153

(22) Filed: Mar. 11, 2020

(65) Prior Publication Data

US 2020/0293887 A1 Sep. 17, 2020

Related U.S. Application Data

(60) Provisional application No. 62/942,644, filed on Dec. 2, 2019, provisional application No. 62/816,880, filed on Mar. 11, 2019.

(51) Int. Cl.
*G06K 9/00* (2022.01)
*G06N 3/084* (2023.01)
(Continued)

(52) U.S. Cl.
CPC .............. *G06N 3/084* (2013.01); *G06N 3/08* (2013.01); *G06V 10/764* (2022.01);
(Continued)

(58) Field of Classification Search
CPC ...... G06N 20/20; G06N 3/006; G06N 3/0454; G06N 5/02; G06N 3/084; G06N 3/08;
(Continued)

(56) References Cited

U.S. PATENT DOCUMENTS 5,920,644 A 7/1999 Fujimoto et al.
8,275,175 B2 9/2012 Baltatu et al.
(Continued)

FOREIGN PATENT DOCUMENTS

EP 2854059 A2 4/2015
WO WO-2019018732 A1 * 1/2019 ............. G06F 16/20
WO WO-2021158313 A1 * 8/2021

OTHER PUBLICATIONS

W. Shi, M. S. Pattichis, S. Celedón-Pattichis and C. LópezLeiva, "Robust Head Detection in Collaborative Learning Environments Using AM-FM Representations," 2018 IEEE Southwest Symposium on Image Analysis and Interpretation (SSIAI), Las Vegas, NV, USA, 2018, pp. 1-4, doi: 10.1109/SSIAI.2018.8470355. (Year: 2018).*

(Continued)

*Primary Examiner* — Andrew M Moyer
(74) *Attorney, Agent, or Firm* — HAYNES BEFFEL & WOLFELD LLP; Ernest J. Beffel, Jr.; Korbin S Van Dyke

(57) ABSTRACT

Method and system with federated learning model for health care applications are disclosed. The system for federated learning comprises multiple edge devices of end users, one or more federated learner update repository, and one or more cloud. Each edge device comprises a federated learner model, configured to send tensors to federated learner update repository. Cloud comprises a federated learner model, configured to send tensors to federated learner update repository. Federated learner update repository com-
(Continued)

prises a back-end configuration, configured to send model updates to edge devices and cloud.

20 Claims, 18 Drawing Sheets

(51) Int. Cl.
    G16H 70/60        (2018.01)
    G06N 3/08         (2023.01)
    G06V 10/764       (2022.01)
    G06V 10/80        (2022.01)
    G06V 10/94        (2022.01)
    G06V 10/96        (2022.01)

(52) U.S. Cl.
    CPC .......... *G06V 10/809* (2022.01); *G06V 10/945* (2022.01); *G06V 10/95* (2022.01); *G06V 10/96* (2022.01); *G16H 70/60* (2018.01)

(58) Field of Classification Search
    CPC ........ G06N 3/045; G06N 3/047; G06N 3/088; G06N 7/023; G06N 3/063; G06V 10/95; G06V 10/96; G06V 10/764; G06V 10/809; G06V 10/945; G06K 9/6253; G16H 70/60; G16H 30/40; G16H 50/20; G06F 18/2413; G06F 18/254
    USPC ........... 706/2, 5–6, 14–16, 25; 382/155–157, 382/159, 305–307, 217–219
    See application file for complete search history.

(56) References Cited

U.S. PATENT DOCUMENTS

| | | | |
|---|---|---|---|
| 8,543,428 | B1 | 9/2013 | Jones, III et al. |
| 9,147,133 | B2 | 9/2015 | Fujimura |
| 9,839,376 | B1 | 12/2017 | Ross et al. |
| 10,423,773 | B1* | 9/2019 | Huang ................ G06N 3/0454 |
| 10,938,852 | B1 | 3/2021 | Streit |
| 11,177,960 | B2 | 11/2021 | Sly et al. |
| 2006/0206724 | A1 | 9/2006 | Schaufele et al. |
| 2011/0172499 | A1 | 7/2011 | Simons-Nikolova et al. |
| 2011/0291834 | A1 | 12/2011 | Boldyrev et al. |
| 2012/0162404 | A1 | 6/2012 | Howell et al. |
| 2013/0046761 | A1 | 2/2013 | Soderberg et al. |
| 2013/0266195 | A1 | 10/2013 | Shiell et al. |
| 2014/0089954 | A1 | 3/2014 | Sampathkumaran et al. |
| 2014/0115515 | A1 | 4/2014 | Adams et al. |
| 2015/0178590 | A1 | 6/2015 | Noma et al. |
| 2015/0213207 | A1 | 7/2015 | Amarasingham et al. |
| 2015/0254890 | A1 | 9/2015 | Noma et al. |
| 2015/0324686 | A1 | 11/2015 | Julian et al. |
| 2015/0339523 | A1 | 11/2015 | Tsunematsu |
| 2015/0363709 | A1 | 12/2015 | Kamei et al. |
| 2016/0253549 | A1 | 9/2016 | Ramic |
| 2016/0328253 | A1 | 11/2016 | Majumdar |
| 2017/0011280 | A1 | 1/2017 | Soldevila et al. |
| 2017/0206691 | A1 | 7/2017 | Harrises et al. |
| 2018/0289334 | A1 | 10/2018 | De Brouwer et al. |
| 2018/0330061 | A1 | 11/2018 | Amiel et al. |
| 2019/0082211 | A1 | 3/2019 | Vats |
| 2019/0244108 | A1 | 8/2019 | Meyerson et al. |
| 2019/0319977 | A1 | 10/2019 | Gottschlich et al. |
| 2019/0354846 | A1 | 11/2019 | Mellempudi et al. |
| 2020/0082062 | A1 | 3/2020 | Mequanint et al. |
| 2020/0110968 | A1* | 4/2020 | Onodera ................ G10L 17/10 |
| 2020/0221191 | A1 | 7/2020 | Baughman et al. |
| 2021/0057106 | A1 | 2/2021 | Chin et al. |
| 2021/0110417 | A1* | 4/2021 | Lade ................ G06Q 30/0275 |
| 2021/0141896 | A1 | 5/2021 | Streit |
| 2021/0326422 | A1 | 10/2021 | Sly et al. |
| 2021/0326433 | A1 | 10/2021 | Sly et al. |
| 2021/0328801 | A1 | 10/2021 | Sly et al. |
| 2022/0012637 | A1* | 1/2022 | Rezazadegan Tavakoli ................ G06N 3/088 |
| 2022/0078626 | A1* | 3/2022 | Doshi ................ G06N 3/08 |
| 2022/0188659 | A1 | 6/2022 | Krasnoslobodtsev et al. |

OTHER PUBLICATIONS

Brisimi, Theodora S., et al. "Federated learning of predictive models from federated electronic health records." International journal of medical informatics 112 (2018): 59-67. (Year: 2018).*
U.S. Appl. No. 15/946,629—Office Action dated May 20, 2020, 10 pages.
Kocabey, Enes, et. al., "Face to BMI Using Computer Vision to Infer Body Mass Index on Social Media", 2017, 4 pages.
U.S. Appl. No. 15/946,629—Response to Office Action dated May 20, 2020, filed Aug. 20, 2020, 13 pages.
U.S. Appl. No. 15/946,629—Office Action dated Oct. 23, 2020, 9 pages.
U.S. Appl. No. 15/946,629—Notice of Allowance dated Jan. 22, 2021, 16 pages.
U.S. Appl. No. 16/802,485—Notice of Allowance dated Feb. 18, 2021, 10 pages.
Wen, Lingyun, et. al., "A computational approach to body mass index prediction from face images", Feb. 9, 2013, 9 pages.
Parkhi, Omkar M., et. al., "Deep Face Recognition", 2015, 12 pages.
Parkhi, Omkar M., et. al., Visual Geometry Group, 4 pages, [Retrieved on Apr. 18, 2021], Retrieved from the Internet < URL: https://www.robots.ox.ac.uk/~vgg/software/vgg_face/>.
Wikipedia, "Diffie-Hellman key exchange", 12 pages [Retrieved on Apr. 18, 2021], Retrieved from the Internet < URL: https://en.wikipedia.org/wiki/Diffie-Hellman_key_exchange>.
WhatIs.com, "What is Diffie-Hellman Key Exchange?", Mar. 2019, 5 pages, [Retrieved on Apr. 18, 2021], Retrieved from the Internet < URL: https://searchsecurity.techtarget.com/definition/Diffie-Hellman-key-exchange>.
Kallam, Sivanagaswathi, "Diffie-Hellman:Key Exchange and Public Key Cryptosystems", Sep. 30, 2015, 27 pages.
Xie, Renjie et al., "A Deep Information-theoretic Framework for Robust Biometric Recognition", Feb. 23, 2019, 7 pages.
U.S. Appl. No. 17/235,871—Office Action dated Jun. 24, 2021, 8 pages.
"Diffie-Hellman Key Exchange", 1 page, [Retrieved on Mar. 18, 2021], Retrieved from the Internet < URL: https://i.stack.imgur.com/AEx0X.png>.
Abozaid Anter et al.,"Multimodal biometric scheme for human authentication technique based on voice and face recognition fusion", Multimedia Tools and Applications, Kluwer Academic Publishers, Boston, US, vol. 78, No. 12, Dec. 15, 2018 (Dec. 15, 2018), pages.
Suwon Shon et al,"Noise-tolerant Audio-visual Online Person Verification using an Attention-based Neural Network Fusion", arxiv.org, Cornell University Library, 201 Olin Library Cornell University Ithaca, NY 14853, Nov. 27, 2018 (Nov. 27, 2018).
Marras Mirko et al, "Deep Multi-biometric Fusion for Audio-Visual User Re-Identification and Verification", Jan. 25, 2020 (Jan. 25, 2020), Advances in Intelligent Data Analysis XIX; [Lecture Notes in Computer Science; Lect.Notes Computer], Springer International Publishing, Cham, pp. 136-157.
Oloyede Muhtahi R O. et al,"Unimodal and Multimodal Biometric Sensing Systems—A Review", IEEE Access, vol. 4, Sep. 16, 2016 (Sep. 16, 2016), pp. 7532-7555.
PCT/US2021/028470 Partial Search Report dated Jul. 23, 2021, 12 pages.
PCT/US2020/045018—International Search Report and Written Opinion dated Dec. 14, 2020, 17 pages.
PCT/US2020/062906—International Search Report and Written Opinion dated Apr. 8, 2021, 10 pages.
Bertoldi et al, "QueryOR: a comprehensive web platform for genetic variant analysis and prioritization", BMC Bioinformatics, Biomed Central Ltd., London, UK, vol. 18, No. 1, Apr. 28, 2017, pp. 1-11, XP021244576, DOI: 10.1186/S12859-017-1654-4.

(56) References Cited

OTHER PUBLICATIONS

Fiume—"System for Interpretation of Personal Genomes," Jan. 1, 2015, XP055494359, ISBN: 978-1-339-35927-4, retrieved from the Internet: URL: https://tspace.library.utoronto.ca/bitstream/1807/69278/3/Fiume_Marc-201506_PhD_thesis.pdf.

U.S. Appl. No. 17/235,889—Notice of Allowance dated Jul. 12, 2021, 3 pages.

U.S. Appl. No. 17/235,876 Notice of Allowance, dated Jan. 12, 2022, 18 pages.

U.S. Appl. No. 17/235,889—Notice of Allowance dated Jul. 7, 2021, 28 pages.

U.S. Appl. No. 17/235,876—Office Action dated Sep. 9, 2021, 25 pagesa.

Bonawitz et. al., Towards Federated Learning at Scale: System Design, Proceedings of the 2nd SysML Conference, dated Mar. 22, 2019, 15 pages.

Thakore, Spark Accelerated Genomics Processing, doc.ai, dated May 7, 2019, 17 pages.

PCT/US2020/022200 International Preliminary Report on Patentability, dated Sep. 23, 2021, 10 pages.

McMahan et. al., Communication-Efficient Learning of Deep Networks from Decentralized Data, Proceedings of the 20th International Conference on Artificial Intelligence and Statistics (AISTATS) 2017, dated Feb. 28, 2017, 11 pages.

U.S. Appl. No. 17/235,871—Response to Office Action dated Jun. 24, 2021, filed Sep. 23, 2021, 10 pages.

U.S. Appl. No. 17/235,871—Notice of Allowance, dated Oct. 5, 2021, 5 pages.

U.S. Appl. No. 17/235,876—Response to Office Action dated Sep. 9, 2021, filed Dec. 8, 2021, 9 pages.

PCT/US2021/028470 International Search Report and Written Opinion, dated Sep. 13, 2021, 17 pages.

U.S. Appl. No. 16/802,485—Notice of Allowance dated Jun. 2, 2021, 10 pages.

PCT/US2021/028470 International Preliminary Report on Patentability, dated Nov. 3, 2022, 12 pages.

\* cited by examiner

Core Template of Machine Learning Workflow

1-N Clinical Trials

Live Model Building Adaptive / Continuously Learning Trial

Trials (Phase 2/3)

Adaptive/Learning Trials

SYSTEM AND METHOD WITH FEDERATED LEARNING MODEL FOR MEDICAL RESEARCH APPLICATIONS

PRIORITY APPLICATIONS

This application claims priority to or the benefit of U.S. Provisional Patent Application No. 62/816,880 titled, "SYSTEM AND METHOD WITH FEDERATED LEARNING MODEL FOR MEDICAL RESEARCH APPLICATIONS," filed Mar. 11, 2019; and U.S. Provisional Patent Application No. 62/942,644 titled, "SYSTEMS AND METHODS OF TRAINING PROCESSING ENGINES," filed Dec. 2, 2019. The provisional applications are hereby incorporated by reference for all purposes.

INCORPORATIONS

The following materials are incorporated by reference as if fully set forth herein:

U.S. Provisional Patent Application No. 62/883,639, titled "FEDERATED CLOUD LEARNING SYSTEM AND METHOD," filed on Aug. 6, 2019;

U.S. Provisional Patent Application No. 62/481,691, titled "A METHOD OF BODY MASS INDEX PREDICTION BASED ON SELFIE IMAGES," filed on Apr. 5, 2017;

U.S. Provisional Patent Application No. 62/671,823, titled "SYSTEM AND METHOD FOR MEDICAL INFORMATION EXCHANGE ENABLED BY CRYPTO ASSET," filed on May 15, 2018;

Chinese Patent Application No. 201910235758.60, titled "SYSTEM AND METHOD WITH FEDERATED LEARNING MODEL FOR MEDICAL RESEARCH APPLICATIONS," filed on Mar. 27, 2019;

Japanese Patent Application No. 2019-097904, titled "SYSTEM AND METHOD WITH FEDERATED LEARNING MODEL FOR MEDICAL RESEARCH APPLICATIONS," filed on May 24, 2019; and U.S. Nonprovisional patent application Ser. No. 15/946,629, titled "IMAGE-BASED SYSTEM AND METHOD FOR PREDICTING PHYSIOLOGICAL PARAMETERS," filed on Apr. 5, 2018.

TECHNICAL FIELD

The disclosed system and method are in the field of machine learning. To be more specific, in the field of federated machine learning utilizing computation capability of edge devices and a federated learning ("FL") aggregator, which is typically cloud-based, relative to the edge devices. In this context, edge devices typically are mobile devices, but also can include nodes that aggregate data from multiple users.

BACKGROUND

Traditional software (1.0) uses declarative inputs and follows deterministic trees of logic, but machine learning (2.0) deals with noisy inputs and uses probabilities. Since the beginning of epistemology, there have been two theories, top-down (Plato theory) and bottom-up (Aristotle theory). Top-down deep learning starts from a theory, not from the data. Bayesian logic combines generative models and probability theory to calculate just how likely it is that the particular answer is true given the data. Bottom up deep learning starts from the data, not the theory. It consists of labeling large amounts of data (both "right" and "wrong" data) to determine association and build a foundation for pattern recognition. It can even learn unsupervised, detecting patterns in data with no labels at all and identify clusters (factor analysis).

The year of 2013 to 2016, the era of the renewed interest in machine learning technology, was followed by the era of deep learning technology, spanning 2016 to the priority filing of this application in 2019. 2019 leads us to the next deep dive of intelligent and/or neuromorphic computing, the federated learning technology.

With machine learning, humans enter input examples and desired output, sometimes called ground truth, and a system learns. Thereafter, output comes from a trained classifier or network. The classifier or network does not have to be programmed directly, but the semantics by which it is generated are programmed. This way, humans train a classifier or network to encode complex behavior with parameters that can be thought of as rules of low complexity. Although the algorithm does not need to be programmed, these neuron networks still need to be trained by humans. They need the input data to be presented in a structured way. Hence, there is a lot of human-aided labor involved in collecting, cleaning, and labeling data. Human talent also is applied to evaluating a model and steering its training in the right direction.

Deep learning applies multi-layered networks to data. While training can be automated, there remains the problem of assembling training data in the right formats and sending data to a central node of computation with sufficient storage and compute power. In many fields, sending personally identifiable, private data to any central authority causes worries about data privacy, including data security, data ownership, privacy protection and proper authorization and use of data.

In the following discussion, the technology disclosed includes systems and methods for federated learning.

SUMMARY

In one application of the technology disclosed, a crowd of end users runs application programs on mobile devices that collect data, train, compute, and evaluate data stored on the mobile devices. The original data does not leave the device where it is stored, that is used to compute an updated model. Devices later federate data globally by sending "derived insights" in the form of updated model parameters, sometimes called tensors, to an FL aggregator where all these derived insights are combined. Devices then receive from the FL aggregator an updated matrix or model which can improve local prediction of these devices. This is repeated in cycles.

With federated learning, a device on the edge can send de-identified updates to a model instead of sending over raw data such as images or audio, that would then be used to update the model. As a result, federated learning greatly privacy concerns, since the raw data never leaves these devices. Federated learning reduces data ownership concerns, as end users are enabled to opt in or out to share raw data and parameter updates created in their devices. Federated learning further greatly reduces security concern, because there is no single point at which a security breach can compromise a large body of data—hackers cannot hack millions of mobile devices that store the raw data.

The machine learning process can be described as five steps. First, a cost function, e.g., how well the network solves the problem, which the system should strive to minimize, is defined. Second, the network is run and see how it does, as measured by the cost function. Third, the values of the network parameters are adjusted, and the network is run again. Fourth, the difference between successive results is the direction or slope in which the result of applying network moved between the trials. This process is called a gradient. Fifthly, if the slope is downhill the parameters are adjusted to move the result changed in downhill direction, and if the slope is uphill, the parameters are changed to move the result in the opposite direction. Steps three to five are repeated. They may be repeated a fixed number of time or until there is limited or no improvement.

The technology disclosed includes a system for federated learning utilizing computation capability of edge devices in communication with an FL aggregator. The system comprises multiple edge devices of end users, one or more federated learner update repositories, and one or more FL aggregators. Each edge device comprises a federated learner model, configured to send tensors to at least one FL aggregator or federated learner update repository.

An FL aggregator includes a federated learner, which may be part of the FL aggregator or a separate module. The FL aggregator and/or federated learner is configured to send tensors to the federated learner update repository. Federated learner update repository comprises a back-end configuration, configured to send model updates to edge devices. Of course, description of constituent parts of the FL aggregator is for purposes of explanation and not to constrain the configuration or scope of the technology disclosed.

The technology disclosed includes is a method of federated learning utilizing computation capability of edge devices. The method comprises sending out tensors by multiple edge devices with federated learning models, receiving tensors by an FL aggregator including a federated learning update repository from the edge devices, distributing updated models from the federated learning update repository to the edge devices, and the edge devices using the updated models.

The technology disclosed includes a federated learning system comprising multiple federated learners, whereas each federated learner is configured to be an end user side library, built for an edge device environment. Such federated learners on edge devices update model parameters based on raw data and ground truth collected in the edge device. The edge devices perform model post-processing and share updated parameters with a central federated learner update repository. The edge devices can download of updated models. They can evaluate the updated models against locally held data, preferably data withheld from training, and report evaluations to the repository or FL aggregator.

The technology disclosed includes a federated learner update repository, sometimes described as a component of an FL aggregator, comprising a federated learning back-end that collects model updates and evaluations from Flea end users. The FL aggregator can be a high availability system. It organizes models that can be updated based on data from end user edge device updates and performs operations required to make these updates, such as admitting or rejecting proposed updates from end users based. Such determination can be based on criteria and metadata sent by end user. The FL aggregator combines admissible end user updates into an overall update and redistributes the updated model to edge devices.

This summary is provided to efficiently present the general concept of the technology disclosed and should not be interpreted as limiting the scope of the claims.

BRIEF DESCRIPTION OF THE DRAWINGS

For purpose of facilitating understanding of the embodiments, the accompanying drawings and description illustrate embodiments thereof, its various structures, construction, method of operation, and many advantages that may be understood and appreciated. According to common practice, the various features of the drawings are not drawn to scale. To the contrary, the dimensions of the various features are expanded or reduced for the purpose of explanation and clarity.

DETAILED DESCRIPTION

Figure 1:
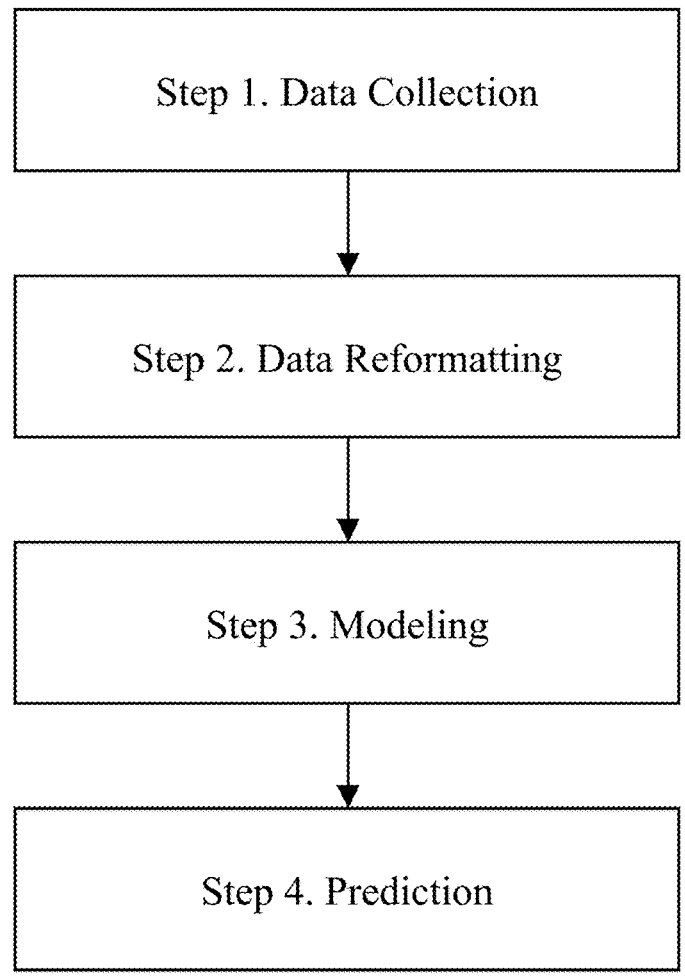
FIG. 1 is a flow chart illustrating an example core template of machine learning workflow.

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information.

For example, it is contemplated that features shown and described with respect to one or more embodiments may also be included in combination with another embodiment even though not expressly shown and described in that specific combination.

For purpose of efficiency, reference numbers may be repeated between figures where they are intended to represent similar features between otherwise varied embodiments, though those features may also incorporate certain differences between embodiments if and to the extent specified as such or otherwise apparent to one of ordinary skill, such as differences clearly shown between them in the respective figures.

Introduction

The technology disclosed includes demonstrated image processing applications for frontal face images and meal images, as well as an anticipated clinical platform. Between the provisional filing of this application and the non-provisional conversion, Applicant applied federated learning to its mobile device app that estimates age, sex, height, and weight, then calculates BMI, all from a selfie, a frontal face photograph of the mobile device user. See, e.g., Patent application Ser. No. 15/946,629, filed Apr. 5, 2018, entitled "Image-based system and method for predicting physiological parameters", which is hereby incorporated by reference. Estimated age, sex, height, weight are calculated from the selfie and reported to the user. The user corrects the estimated values. The user's edge device updates model parameters to take into account the ground truth provided by the user. For instance, age might change from 55 to 64 years, weight from 176 to 182, and height from 5'8" to 6'2". This ground truth is backward propagated through a network on the edge device, producing parameter adjustments. Occasionally, the updated parameters are returned to an FL aggregator. The FL aggregator periodically updates and redistributes an updated model.

An anticipated clinical platform also is disclosed. Clinical can be taken in a broad sense to include collection of health related data, such as mood or general health, which might be assessed against a voice or photographic sample. Clinical can also be take in a pharmaceutical sense for providing a tool for contract research organizations to collect data occasionally or periodically during a traditional clinical trial. Collection of data that is partially or completely anonymized can be complemented with a so-called synthetic control arm, in lieu of giving part of the trial participants a placebo. Anonymized data can encourage frequent reporting. Receiving test doses, instead of being at risk of receiving a placebo, is further encouraging.

Mobile machine learning, in this disclosure, refers to inference on device, training on device, and federated learning, which can be applied to health care. Theoretical and practical challenges need to be faced and overcome to demonstrate a practical federated learning application, especially in a sensitive area such as health care.

Figure 8:
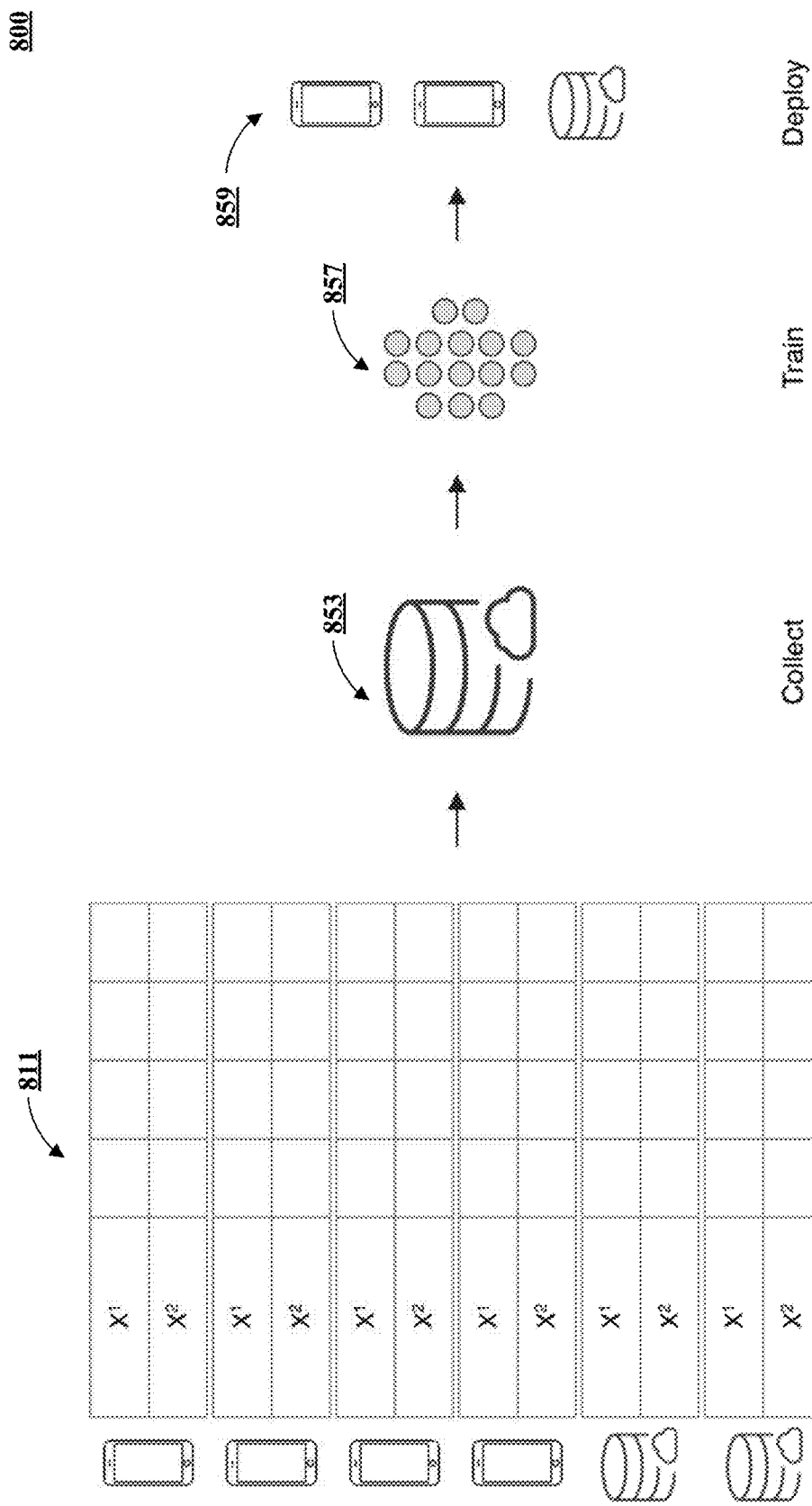
FIG. 8 is a diagram illustrating centralized data collection and training, leading to deployment to edge devices.

A typical machine learning workflow is illustrated by FIG. 8. Having identified a problem space and a learning task, one finds a large body of data 811, 853 to train a model at a central repository 857, in a centralized manner. After being satisfied with the model, one deploys it to edge devices or to a cloud-based compute resource 859 for prediction. Typical model training involves centrally collecting the data and centrally training the model even when it is deployed in a distributed manner. This involves bringing the data 811 to a central repository 853 to gain control over how it's used in training 857.

Federated Learning

FIG. 1 is a high level flow chart of machine learning workflow.

In some embodiments, a core template of machine learning workflow comprises four steps. Step 1 is data collection, to procure raw data. Step 2 is data re-formatting, to prepare the data in the right format. Step 3 is modeling, to choose and apply a learning algorithm. Step 4 is predictive analytics, to make a prediction. Variables that are likely to influence future events are predicted. Parameters used to make the prediction are represented in multi-dimensional matrix, called tensors.

A multi-dimensional matrix, or tensor, has certain features commend this data representation to machine learning. Linear algebra operations are efficiently applied by GPUs and other parallel processors on computers. Linearization or differentiation make it feasible to frame optimization problems as linear algebra problems. Big data is difficult to process at scale without tensors, so many software tools have come onto market that simplify tensor computing, e.g., TensorLab, Matlab package, Google TensorFlow, etc. Hardware is following software. Groups of engineers are working on tensor processing accelerator chips, e.g., NVDIA GPUs, Google TPUs, Apple A11, Amazon Inferentia, Graviton and Echo-chip, Facebook Glow, and a whole range of technology companies that make Application-Specific Integrated Circuits (ASIC), field programmable gate arrays (FPGAs) and coarse-grained reconfigurable arrays (CGRAs) adapted to calculate tensors with tensor calculation software.

Figure 2:
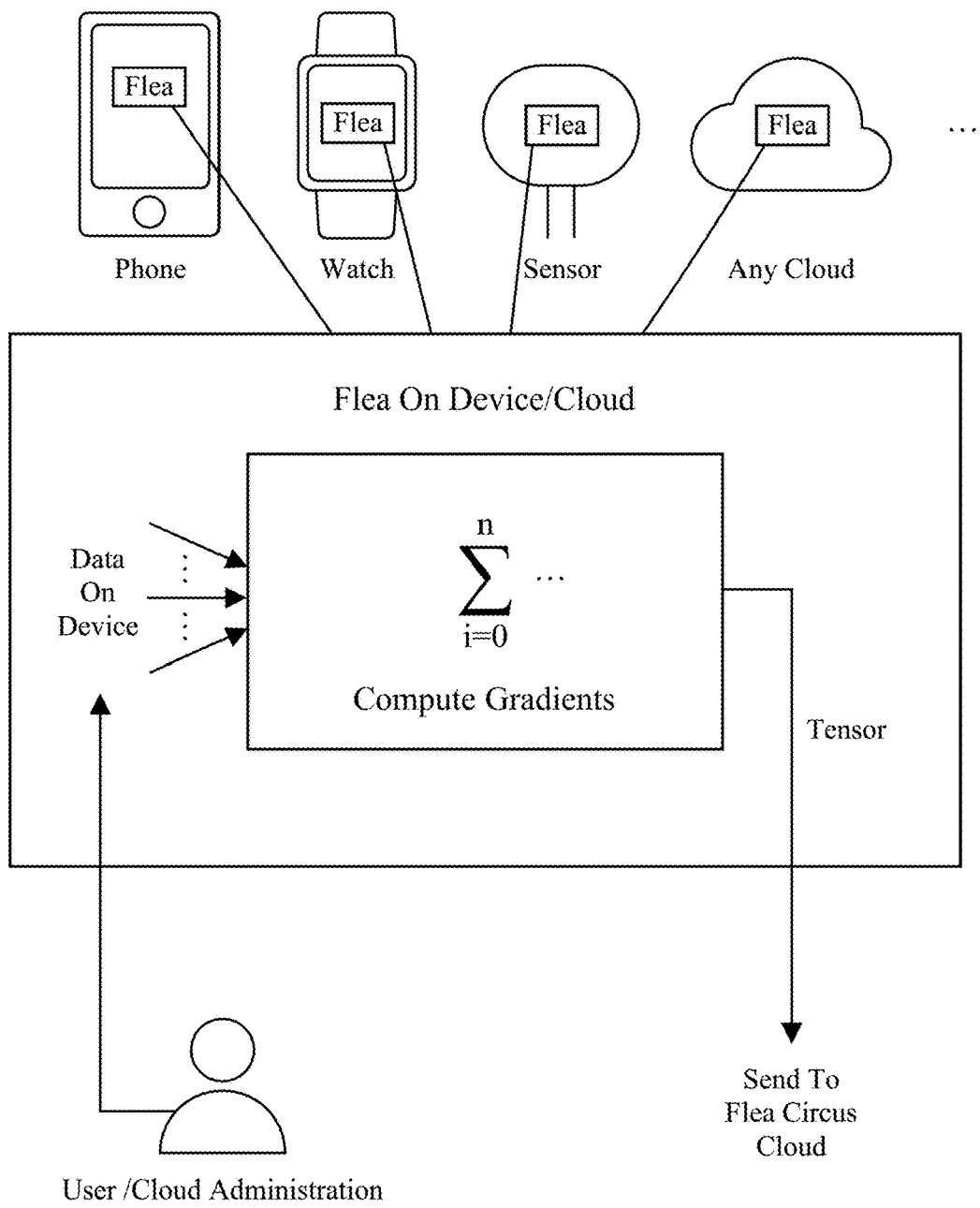
FIG. 2 is a diagram illustrating an example federated learning model with multiple edge devices and a central FL aggregator.

FIG. 2 is a diagram illustrating an example federated learning model with multiple edge devices and a central FL aggregator.

A federated learner (Flea) can be implemented as an end user side library, built for an edge device environment, to perform local model update calculations using data collected in the edge device environment. The Flea can perform post-processing after model updating, including applying perturbations (e.g., encryption and introduction of noise for privacy purposes), sharing the model update with a central update repository (i.e., an FL aggregator), optionally downloading updated models, evaluating updated models, and sharing evaluation metrics across platforms, e.g., Flea-iOS (for iPhones), Flea-Android (for Android phones), Flea-kubernetes (for node clients), etc.

In a federated workflow 915, we start with a base model 951 that may have been trained in this conventional manner. Once this base model 951 is trained, refinement can proceed without centrally collecting any further data. Instead, the base model is distributed to individual devices 953. These edge devices perform local training to generate local model updates 957, using data (not shown) that is on those devices. The federated workflow aggregates the local updates into a new global model 959 which will become our next base model 951 that will be used for inference and additional rounds 915 of training a federated loop. Again, updating via the federated loop 915 does not require centrally collecting data. Instead, we're sending the model to the data for training, not bringing data to the model for training. This is a decentralized workflow instead of a centralized workflow.

Health Care Space

This can be particularly helpful when dealing with sensitive data, such as medical information in the health care space. In this space, there are a number of issues around data sensitivity. It is crucial to address privacy, both to attract participation of individuals who are reluctant to share sensitive medical information and to comply with regulations.

In some circumstances, an individual may understand the research value of sharing information, but doesn't trust the organization that they're being asked to share with. The individual may wonder what third parties that could gain access to their data. On the B2B side, there are intellectual property issues that thwart companies that want to collaborate, but are unable to share their raw data for IP reasons. The technology disclosed can enable collaboration without necessarily sharing data. Also on the B2B side, some companies have internal data policies that prevent even intra-company, cross-division sharing of data. These companies would benefit from collaboration without data sharing.

In the health care space, regulatory concerns can be paramount. The United States has the federal Health Insurance Portability and Accountability Act, HIPPA. The Eurozone has GDRP. Both impose strict rules around how medical data is handled and shared.

The technology disclosed applies federated learning to an environment where it's difficult to share underlying data due to data sensitivity concerns. One of the priority applications addresses so-called vertical learning. This application focuses on so-called horizontal federated learning, in which devices have at a different sample space for the same feature space, as opposed to vertical learning, which can be applied to the same sample space with different feature spaces. Horizontal learning applies well to a mobile environment, where a model can be completely shared.

Figure 10:
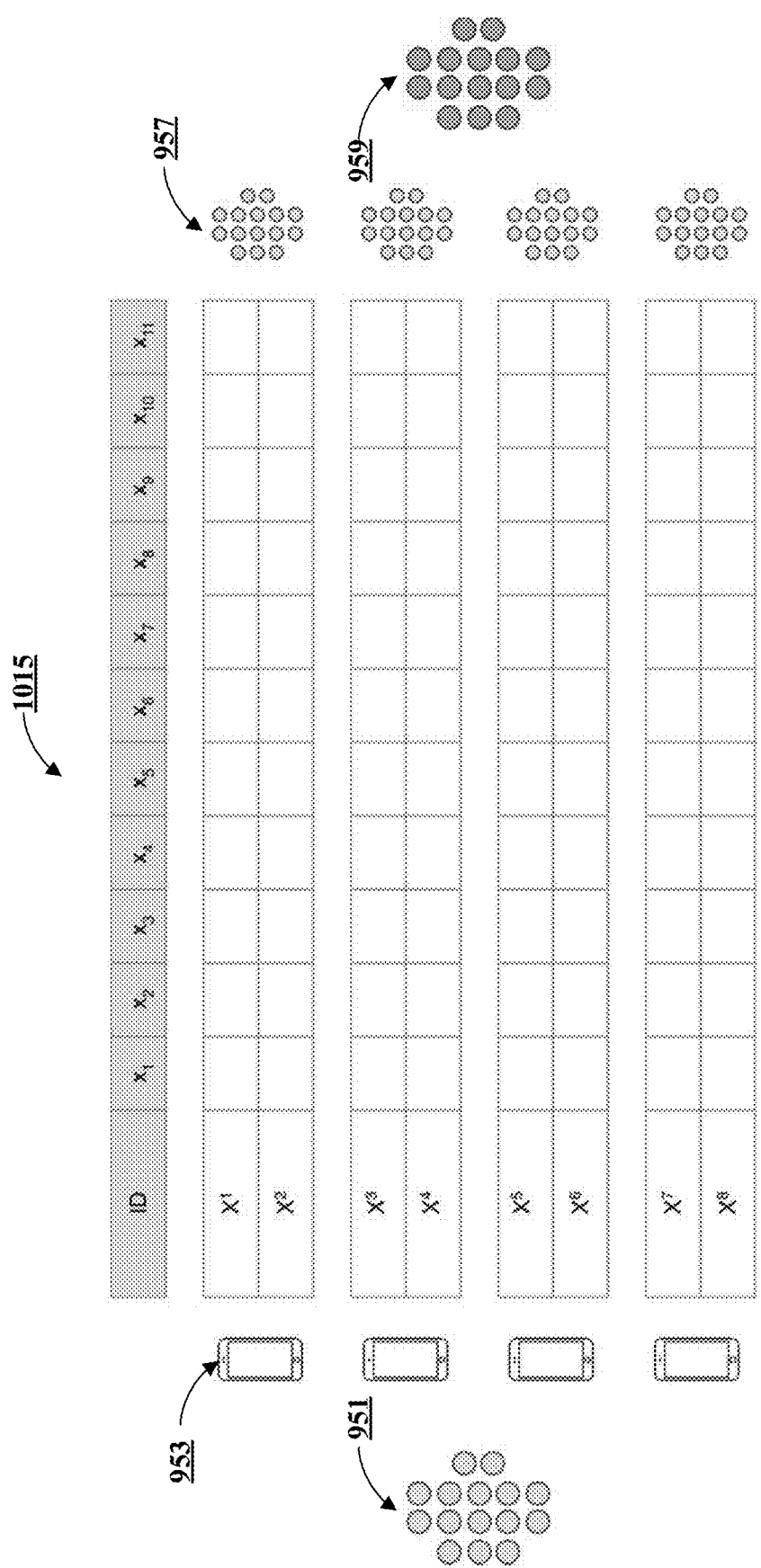
FIG. 10 is a diagram illustrating more detail of data at edge devices during update training.

Consider, with reference to FIG. 10, a data set in the form of a table 1015. This data can be visualized as is a matrix with samples across rows and features down columns. The rows of data may correspond to samples used with a neural network for training. They also may correspond to a SQL-returned table and may have a unique identifiers, IDs, across rows and again have columns of features. In FIG. 10, the dataset 1015 is divided horizontally among devices 953. In this horizontally partitioned dataset, each subset of the data has access to the same feature space, but has its own sample space, as one can imagine of data trained or collection on mobile phones.

Consider an image processing application and a tensor applied to images that are, for example, 224×224 pixels, prior to being sent to a neural network for inference and training by backward propagation. Images on different devices have the same feature space, but they're different images, belonging to different sample spaces. Each edge device can start with the same base model. An FL aggregator or federated learning repository or some other central authority or compute resource sends the base model to the edge device for update training, to produce updated models 957. The edge devices 953 train using respective partitions of the data 1015, producing the updated models 957, which are aggregated 959 into an updated model which can be distributed as a new base model 951. In this process, the base model resides locally on each device. Each device trains locally on data that is available on device. The federated loop aggregates the local updates to produce a new global model.

Figure 11:
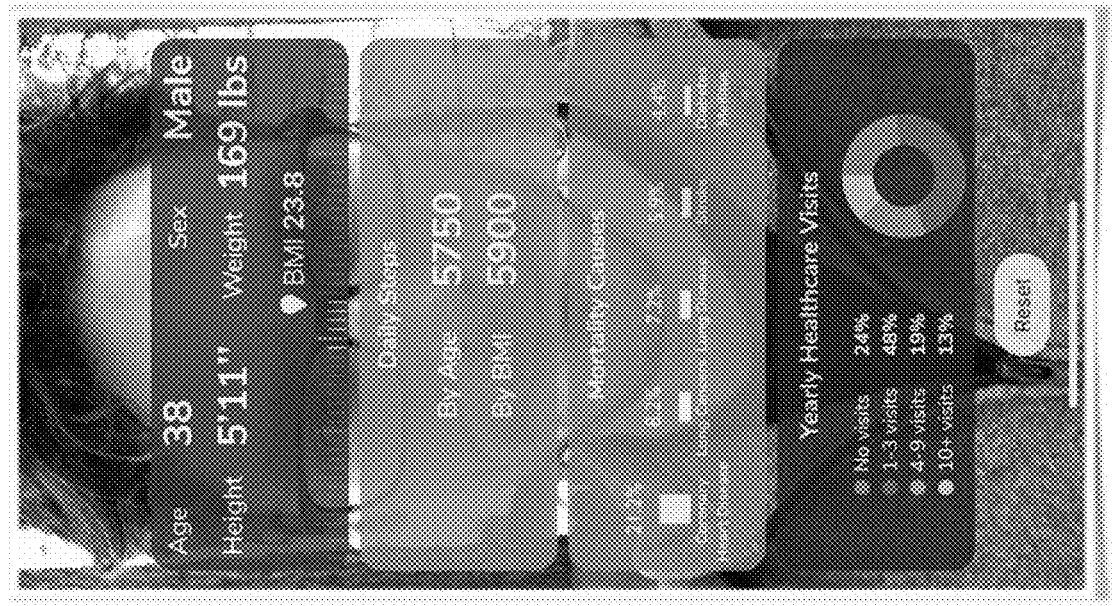
FIG. 11 is a graphic user interface illustrating use of a selfie to estimate age, height and weight, from which body mass index (BMI) can be calculated.
Figure 11:

One working example of horizontal learning executed in a mobile environment is the medical selfie. The medical selfie model infers the user's age, sex, height and weight from a frontal image a user's face. This data can be used to calculate the user's body mass index, BMI, which is a data point in health care statistics. FIG. 11 depicts a graphic user interface for medical selfies. At one time, most of the information in 1153 is collapsed, and the frontal face image is visible. When estimates are given, the user is invited to correct the system's estimates of age, sex, height and weight. (BMI is calculated from the other values.) At another time, the user can expand some or all of the information panels, as in 1157, and reveal further information.

This model can be trained in a federated manner, beginning with a base model 951 trained conventionally on millions of images to produce a model that performs relatively well. This base model is sent to an edge device where it's first used to perform inference on new images collected by the user, such as selfies. The user will be given the option to correct the inferences made by the model, so that accurate age, sex, height and weight are known. With this ground truth, the base model is trained to produce an updated model. Each of the participating edge devices similarly produces local updates to the current model. Those local updates are centrally aggregated into a new based model and the process repeats. Aggregation can be performed using a federated average algorithm, applying the averaging formula 1577 in FIG. 15. This is a weighted average of the updates to the model, weighted according to the number of samples used by an edge device to produce its update. Alternatively, only updates based on a threshold number of samples would be aggregated and the aggregation could be un-weighted. In practice, the base convolution model can be a MobileNet V2 model with supplemental training that builds on transfer learning of facial images. Transfer learning can leverage training on an ImageNet classification problem. For age, sex, height and weight, custom layers can be stacked on top of an ImageNet or MobileNet V2 model.

Figure 9:
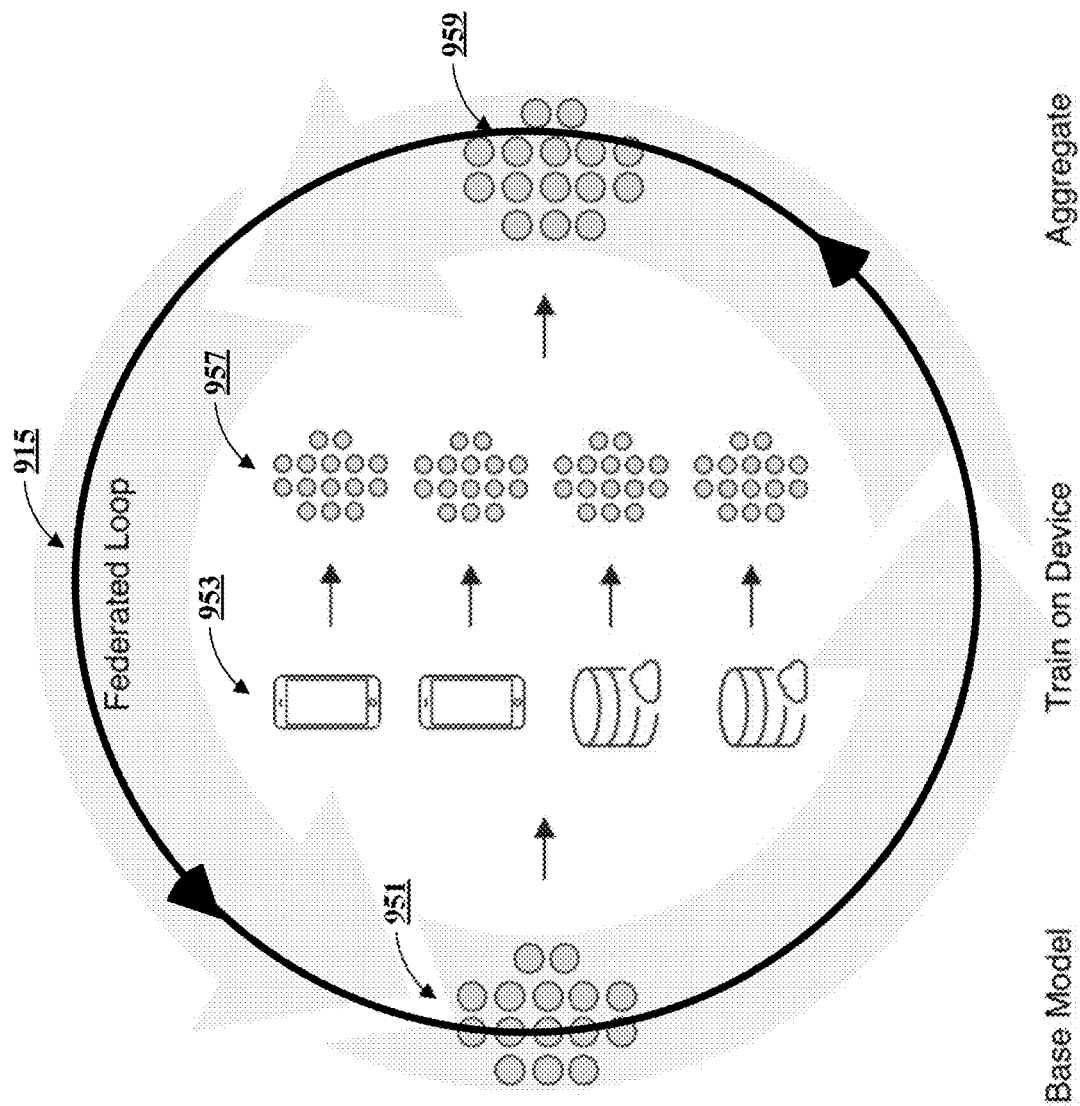
FIG. 9 is a diagram illustrating edge device update training followed by centralized aggregation of the updated models.

Initial training of the base model can be offline. Then, the trained base model can be distributed to edge devices, which produce updates that are processed by the federated loop, as illustrated in FIG. 9. Asynchronous distribution of base models and receipt of proposed updates present significant engineering challenges, which can be explained by flattening the federated loop into a message flow diagram, FIG. 12.

Figure 12:
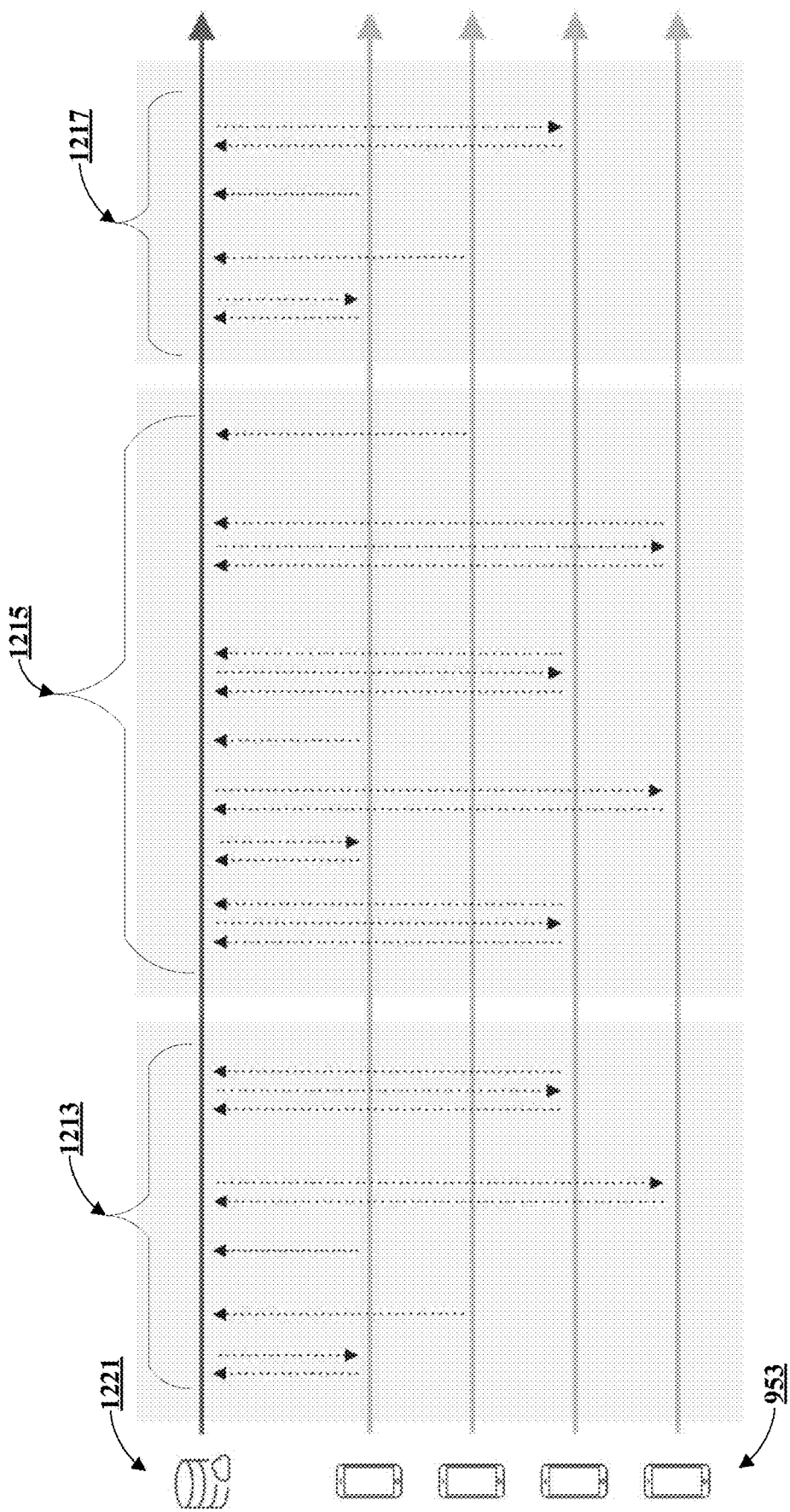
FIG. 12 is a simplified message diagram depicting exchanges between four edge devices and an FL aggregator, over three cycles of model updating.

In FIG. 12, the horizontal axis is time. Devices are depicted on the vertical axis, including a coordinating server 1221 that manages training tasks and performs model aggregation. Below the coordinating server, the figure illustrates four edge devices 953 that perform training using local data to produce local updates of a base model. In the figure, messages travel down and up between the coordinating server 1221 and individual devices 953, each represented by a horizontal line. The stream of communications reflects asynchronous messaging, with simplifications involving just a handful of devices and grouping of communications back and forth that would likely be interleaved or multiplexed. Each of the devices 953, at unassigned times, makes a request to the server 1221, indicating their availability for training tasks, either expressly or implicity. Supposing there are, the server 1221 responds in the affirmative and send an updated, latest version of the model to the device, if it has not already done so. The edge device 953 will train on local data, update its a local model and send the updated version of the model back to the server.

Communications between devices 953 and server 1221 are asynchronous, over network connections, and sometimes unreliable. In some cases, an edge device or client make a request for a training task, but does not receive a response for the server. This can be represented by a upward arrow, for instance near the beginning of cycle 1223, without a responsive downward arrow. In other cases, the client might request and receive an assignment and current model version, but never upload an updated model. In other cases, a client may participate multiple times during a given training cycle. The server 1221 checks to make sure that updates received apply to a current version of the base model, that the edge device is not updating a deprecated base model version. A cycle, such as 1213, 1215 or 1217, eventually reaches a predetermined threshold. This threshold could be expressed as a number of clients that have participated in the round, as a number of training samples processed in the updated models, or as an elapsed amount of time. Each of the cycles corresponds to one round of the federated loop 915 that produces a new global model (959, which becomes 951), and to distribution to the edge devices of the updated, new model. The edge devices can use the new model for predictions and training as additional data is collected. Preferably, the edge devices do not repeatedly train using old data that previously was used to train an updated model that was forwarded to the server 1221 for aggregation. The process repeats, as depicted for three cycles in FIG. 12.

The engineering challenges are significant. One challenge arises from networking issues and latency of devices are joining and leaving the network. Another challenge is that the mobile model is unquantized and includes on the order 20 megabytes of model parameters. It is useful to make sure that the model is not updated too often over cellular data connections. Updating also hits the mobile device's power constraints, as training on a mobile phone is resource intensive and, therefore, power hungry. In some implementations, training is limited to times when the phone is plugged in, has a Wi-Fi connection and is not in otherwise use by the user.

On the server side, asynchronous task management requires record keeping and keeping track of all of the training tasks and local updates in process numerous edge device. It also involves periodically performing aggregation and redeploying updated models. In addition to these engineering challenges, there are theoretical concerns, arising from classical statistics, that can only be overcome by empirical investigation.

Figure 13:
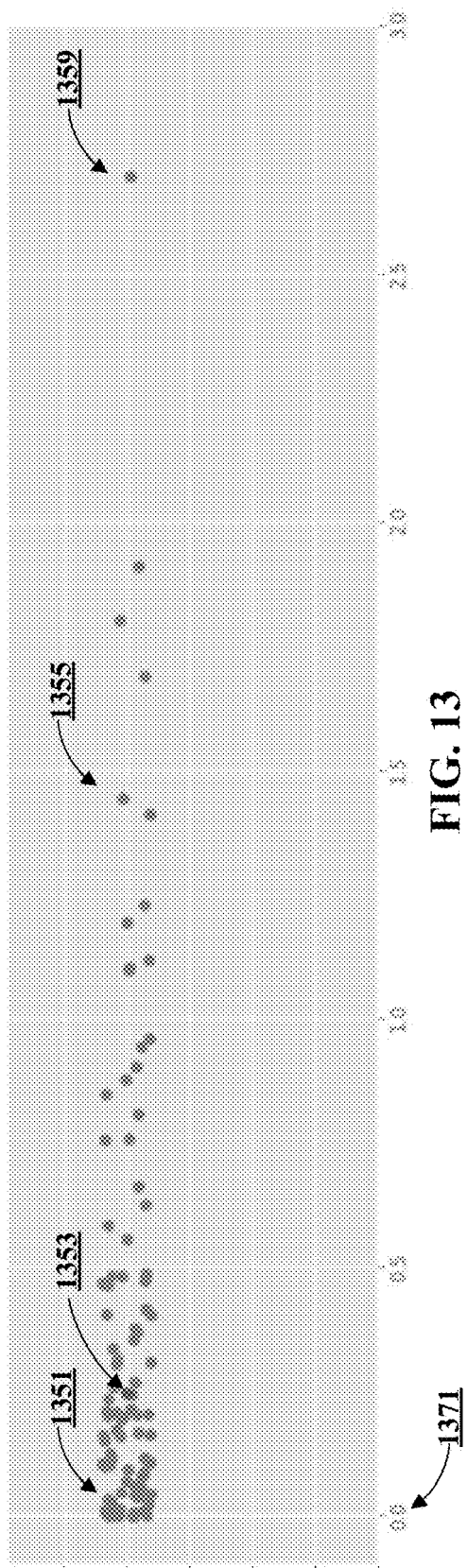
FIGS. 13-14 are scatter plots from edge device training on small samples and a centrally model trained on a large sample.
Figure 14:
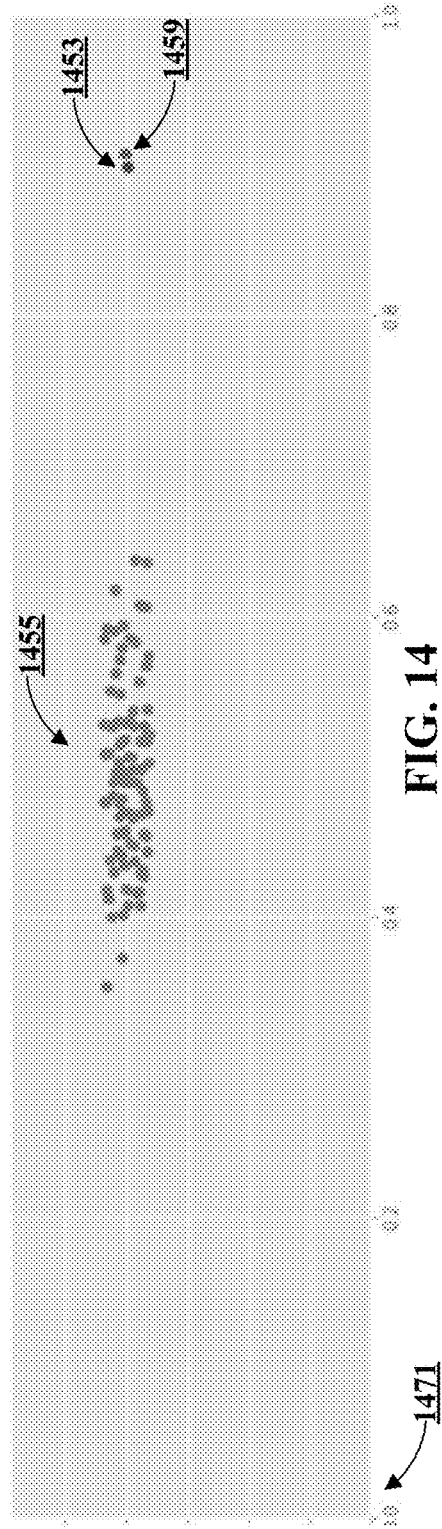

In experiments performed thus far, federated training actually has worked. FIGS. 13-14 illustrate a scatter plot of data from a so-called In'n Out model that was trained to distinguish between photographs taken indoors and out of doors. FIG. 13 plots a loss function, for which a lower value is better, except in case of overtraining. FIG. 14 plots a likelihood of correct binary classification, for which a higher value is better.

The scatterplot in FIG. 13 graphs local losses versus global trading loss for a binary classification test model that deployed internally by Applicant. Towards the left, dot 1353 is the global training loss of the original base model. Other dots clumped to the left 1351 and scattered to the right 1355, 1359, are the local losses of that model trained on individual devices, which sent their models to a server (e.g., 1221). The graph shows two sorts of bad results resulting from training on end devices with small sample sets. First, in some cases, e.g., 1359, the local losses exploding off to the right. This suggests that something has gone badly in training that that caused the gradient descent to jump out of a local minima found during the initial global training. Second, the local loss sometimes dives towards zero, which indicates overfitting of the local training data. This is a recognized issue with small sample sizes, relative to the initial sample size that we used to produce the global model. FIG. 14 depicts the corollary accuracy of the original based model. The accuracy 1453 of the initial base model was roughly 90 percent for a binary classification problem. The local accuracy 1455 is clustered near 50 percent. The updates to the models that are sent back to the server for aggregation, when tested against samples held back for validation, have an accuracy that hovers around 50 percent, between 40 and 60 percent, which suggests that the local updates to the models are no better than random guesses at binary classification.

With excitement, these inventors determined that the federated average of the updated models actually produced a model that was slightly better than the base model before aggregation. The aggregated model loss is represented by a blue dot 1459 just to the right of the red dot 1453. Again, the average of worse models produced an improved, better model. That is extraordinarily counterintuitive, given the position near random chance of cluster 1455.

Figure 15:
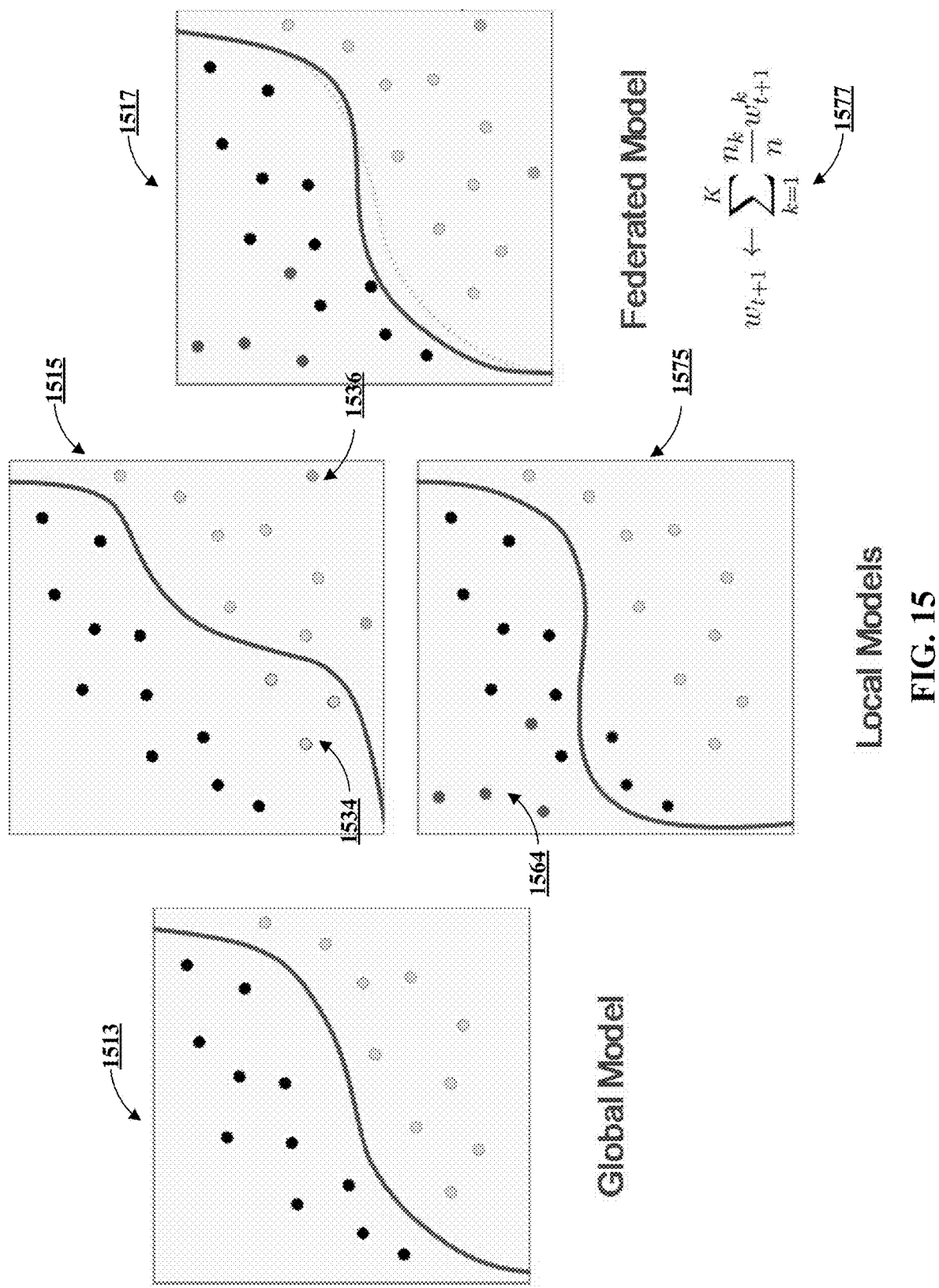
FIG. 15 is a conceptual diagram illustrating updating a global model from local models, applying update averaging.

FIG. 15 is a conceptual depiction, appealing to intuition, why the bad models averaged might work well. Imagine beginning with a base model in a two dimensional space 1513 with a good decision boundary that accurately classifies gray dots, below the line, against black dots, above the line. Then, we send this global model to two devices and train it on those devices, producing the decision boundaries illustrated upper and lower graphs 1515 and 1575. In the upper graph, two yellow dots 1536 and three new gray dots 1534 are added in the bottom half of 1515. The new dots have pulled the decision boundary down and to the right, separating the new dots. In the lower graph 1575, we've added four purple dots 1564 in the top left corner, representing new black samples. The added samples have pulled the decision boundary up and to the left, in the direction of the new dots. In both cases, the resulting a decision boundary that is actually worse, resulting in misclassification of some of the original samples. Counter intuitively, when we average the 1515 and 1575 decision boundaries to produce 1517, which corresponds to averaging the weights 1577 that describe that decision boundary, we end up with a boundary that is close to the original one and that accurately classifies both the original and added samples.

Conceptually, this is what federated averaging is doing. It's able to take updated models, in which decision boundaries that have been pulled in opposite directions, and average them into something closer to the center that improves on a base model. Of course, this is happening in very high dimensional space, with on the order of four million parameters for a MobileNet model. Projecting what happens onto a two-dimensional space helps us develop an intuition for how this might work.

Classical statistics pose additional theoretical challenges to federated learning, as user device data collection and training defeats any guarantee or assumption that training data is independent and identically distributed, IID. This is a distinguishing feature of federated learning. The loss of the strong statistical guarantee allows the system with high dimensionality to make inferences about a wider population of data, including in our training set samples collected by edge devices. Consider the medical selfie example again. We're training the initial model on a library of selfies and sending it to an edge device for training on more selfies, including performing inference on the new selfies. When we send the model to edge device for training, we are potentially exposing it any image that a user can take on a mobile phone. We are no longer training the model on just selfies, but also on kittens and houseplants and sunsets and so on. Exposing the model to a different population than the population than our target population for actual training and inference means that we've lost the strong statistical guarantee that our training will be results will produce results that generalize. To address this, beyond training users, we can filter image capture and updating, before and after data leaves the edge device.

First, the technology disclosed can be enhanced by putting a filter in front of model training, to try to constrain the sample population collected and used for training on edge devices, bringing it closer to the intended target population. Second, we can put a filter at the FL aggregator to threshold out some updates that appear to have been trained on bad data.

The first filter can limit training to images of selfies, instead of exposing it to all kinds of images. A face detector in front of the model does not treat sunrises or house plants as faces. Then, the edge devices are training on any image that has a face in it, which is mostly selfies but could include some other images. That brings us closer to that target population.

On the backside, the technology disclosed can be enhanced by filtering out some of the updates that appear to be very bad. The training that produced wildly divergent updates potentially resulted from being exposed to bad training data or training data that has been mislabeled, such as a typo in a person's weight or height. Consider again our local losses versus our global training loss graph in FIG. 13. Recall that some of these losses, e.g., 1359, explode off to the right. A second filter can eliminate those updates from being averaged into the model, where it appears that the local updated has jumped too far outside of our original local minima.

Intuitively, this corresponds to updated models that have very badly malformed decision boundaries, which could result from bad training data, such as mislabeled training data. In any case, we want to measure some kind of distance between local updates and the original model. One measure would be a simple Euclidean distance across all the weights and a relative to the distribution of distances among local updates in a batch. The distribution can be used to filter out updated modes that are very bad or divergent. This should allow us to restrict our aggregation by federated averaging to updated models that have been trained on a population of data that is similar to our target population.

Empirical results have been good. Internally research by applicant is showing. Actual test deployments also showing good federated learning. Despite the loss of classical IID, strong statistical guarantee, we end up with empirical results that are good. Of course, this depends on class size and sample size as well as hyper-parameters of the model. It also would be impacted by implementation of the filters described. The inventors have concluded that federated learning works and is a viable approach to machine learning for a range of health space tasks.

Another theoretical issue is kinds of privacy guarantees that can be made when federated learning is implemented. Does this approach leak any information about the training data? Can the input be reconstructed from the updates? Two approaches to ensuring privacy during horizontal federated training bear consideration. First, is the practice of adding noise to a statistic to mask its true value. Research has shown that this technique can be applied in both federated and non-federated contexts to mask the participation of a sample or even an entire client in a training room.

Second, homo morphing encryption can be considered. This approach applies a series of computations to a cipher text and then decipher the results and ends up with the same results as if that series of computations had been applied to the original text. However, homo morphing encryption may only work with linear transformations and linear approximations of non-linear transformations.

Overall Approach

Figure 16:
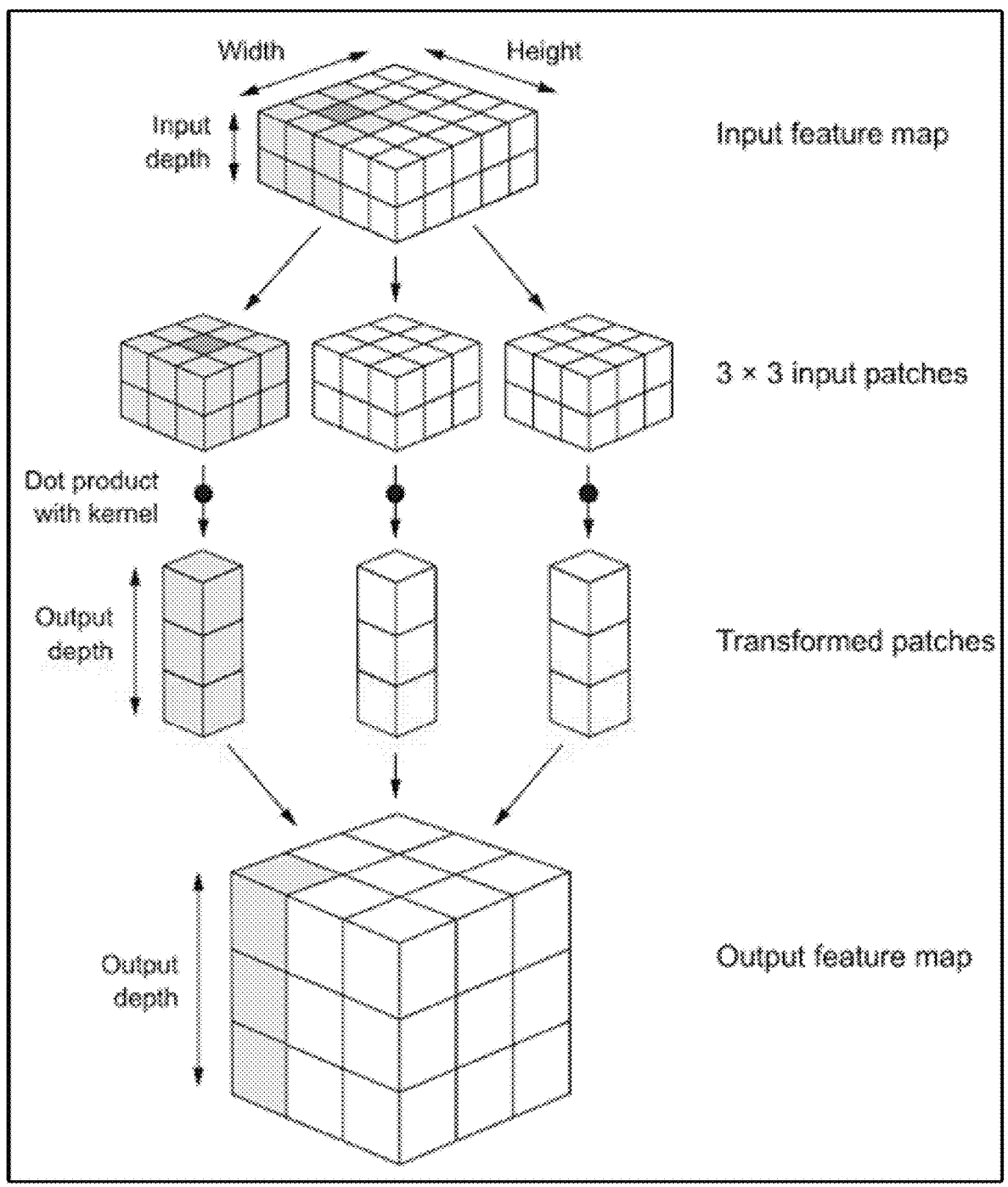
FIG. 16 is an example convolutional neural network.
Figure 17:
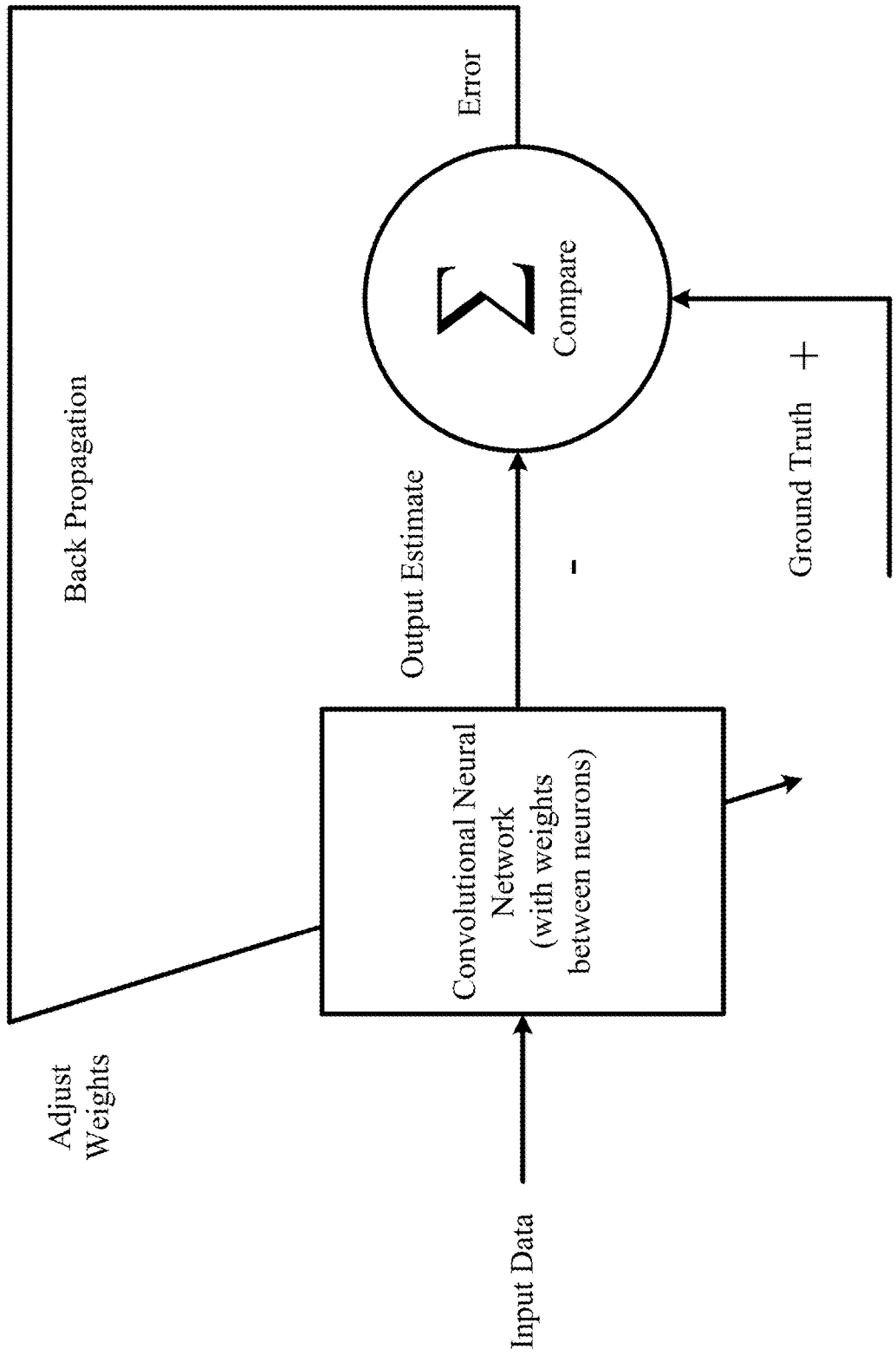
FIG. 17 is a block diagram illustrating training of the convolutional neural network of FIG. 16.

With this example in mind, we return to describing the overall approach. As show in in FIG. 2, Flea end users can communicate and collaborate with one another (potentially in tandem with one or more FL aggregator backends) to build and update models of computation in multiple ways. These configurations are described in the context of medical research use cases. A general discussion of regarding convolutional neural networks, CNNs, and training by gradient descent is facilitated by FIGS. 16-17.

CNNs

A convolutional neural network is a special type of neural network. The fundamental difference between a densely connected layer and a convolution layer is this: Dense layers learn global patterns in their input feature space, whereas convolution layers learn local patters: in the case of images, patterns found in small 2D windows of the inputs. This key characteristic gives convolutional neural networks two interesting properties: (1) the patterns they learn are translation invariant and (2) they can learn spatial hierarchies of patterns.

Regarding the first, after learning a certain pattern in the lower-right corner of a picture, a convolution layer can recognize it anywhere: for example, in the upper-left corner. A densely connected network would have to learn the pattern anew if it appeared at a new location. This makes convolutional neural networks data efficient because they need fewer training samples to learn representations they have generalization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map—the number of filters computed by the convolution. Often these start with a depth of 32, continue to a depth of 64, and terminate with a depth of 128 or 256.

A convolution works by sliding these windows of size 3×3 or 5×5 over the 3D input feature map, stopping at every location, and extracting the 3D patch of surrounding features (shape (window_height, window_width, input_depth)). Each such 3D patch is ten transformed (via a tensor product with the same learned weight matrix, called the convolution kernel) into a 1D vector of shape (output_depth,). All of these vectors are then spatially reassembled into a 3D output map of shape (height, width, output_depth). Every spatial location in the output feature map corresponds to the same location in the input feature map (for example, the lower-right corner of the output contains information about the lower-right corner of the input). For instance, with 3×3 windows, the vector output [i, j, :] comes from the 3D patch input [i-1: i+1, j-1:J+1, :]. The full process is detailed in FIG. 11.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

FIG. 12 depicts a block diagram of training a convolutional neural network in accordance with one implementation of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where $\delta$ = (ground truth) − (actual output)

In one implementation, the training rule is defined as:

$$W_{nm} \leftarrow W_{nm} + \alpha(t_m - \varphi_m) a_n$$

In the equation above: the arrow indicates an update of the value; $t_m$ is the target value of neuron m; $\varphi_m$ is the computed current output of neuron m; $a_n$ is input n; and $\alpha$ is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1+e^{-h}}$$

In the sigmoid function above, h is the weighted sum computed by a neuron. The sigmoid function has the following derivative:

$$\frac{\partial \varphi}{\partial h} = \varphi(1-\varphi)$$

The algorithm includes computing the activation of all neurons in the network, yielding an output for the forward pass. The activation of neuron m in the hidden layers is described as:

$$\varphi_m = \frac{1}{1+e^{-h_m}}$$

$$h_m = \sum_{n=1}^{N} a_n w_{nm}$$

This is done for all the hidden layers to get the activation described as:

$$\varphi_k = \frac{1}{1+e^{h_k}}$$

$$h_k = \sum_{m=1}^{M} \varphi_m v_{mk}$$

Then, the error and the correct weights are calculated per layer. The error at the output is computed as:

$$\delta_{ok} = (t_k - \varphi_k)\varphi_k(1-\varphi_k)$$

The error in the hidden layers is calculated as:

$$\delta_{hm} = \varphi_m(1-\varphi_m)\sum_{k=1}^{K} v_{mk}\delta_{ok}$$

The weights of the output layer are updated as:

$$V_{mk} \leftarrow V_{mk} + \alpha \delta_{ok} \varphi_m$$

The weights of the hidden layers are updated using the learning rate α as:

$$v_{nm} \leftarrow w_{nm} + \alpha \delta_{hm} a_n$$

In one implementation, the convolutional neural network uses a gradient descent optimization to compute the error across all the layers. In such an optimization, for an input feature vector x and the predicted output y, the loss function is defined as l for the cost of predicting ŷ when the target is y, i.e. l (ŷ, y). The predicted output ŷ is transformed from the input feature vector x using function $f$. Function $f$ is parameterized by the weights of convolutional neural network, i.e. $ŷ = f_w(x)$. The loss function is described as l(ŷ, y)=l($f_w$ (x), y), or Q (z, w)=l($f_w$ (x), y) where z is an input and output data pair (x, y). The gradient descent optimization is performed by updating the weights according to:

$$v_{t+1} = \mu v_t - \alpha \frac{1}{n} \sum_{i=1}^{N} \nabla w_t Q(z_t, w_t)$$

$$w_{t+1} = w_t + v_{t+1}$$

In the equations above, α is the learning rate. Also, the loss is computed as the average over a set of n data pairs. The computation is terminated when the learning rate α is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $Z_t$, described as:

$$V_{t+1} = \mu V_t - \alpha \nabla w Q(z_t, w_t)$$

$$W_{t+1} = W_t + V_{t+1}$$

In the equations above: α is the learning rate; μ is the momentum; and t is the current weight state before updating. The convergence speed of SGD is approximately O(1/t) when the learning rate α are reduced both fast and slow enough. In other implementations, the convolutional neural network uses different loss functions such as Euclidean loss and softmax loss. In a further implementation, an Adam stochastic optimizer is used by the convolutional neural network.

Model Exchange in Federated Learning

In some embodiments, Flea end users communicate and collaborate with one another to build and update models, effecting a lateral tensor ensemble of user models, in a one-to-one manner. The end users could also laterally organize their own trials and choose a central FL aggregator to which to send the gradients and get the averaged gradients back in a distributed fashion.

In yet some other embodiments of the disclosure, tensors are configured to function tensorial handshakes, with one-to-one tensors for distributed clinical trials. End users can also laterally organize their own trials and choose a central FL aggregator to send the gradients and get the averaged gradients back in a distributed fashion.

In some embodiments, Flea end users communicate and collaborate with one another to build and update models of computation in tensor economy in a many-to-one manner. Tensors for distributed clinical trials. Each end user can be called upon several sponsors to conduct several trials at the same time and can use the same underlying data to create new tensors.

In yet some other embodiments of the disclosure, there are many-to-one tensors for distributed clinical trials. Each end users can be called upon several sponsors to conduct several data trials at the same period of time.

In some embodiments, Flea end users communicate and collaborate with one another to build and update models in autonomous tensor ensembles, in a many-to-many manner. Just as algorithms start to write themselves, devices without human intervention will start to collect information between each other. These will just behave like many insect species, including ants and bees, who work together in colonies, and their cooperative behavior determines the survival of the entire group. The group operates like a single organism, with each individual in a colony acting like a cell in the body and becomes a "superorganism". Federated Deep learning only needs these small players like insects, ants, critters and bees to create big and smart things with immense, complex and adaptive social power and ambitious missions.

In yet some other embodiments of the disclosure, there are many-to-many tensors for distributed clinical trials. Just as algorithms start to write themselves, devices are configured to collect information between each other without human intervention. Cheap Micro-Computer Units can soon be deployed anywhere, without mains, docking, or battery replacement. MCUs can be configured to behave like many insect species, including ants and bees, who work together in colonies. The cooperative behavior of the group of MCUs determines the survival of the entire group. The group operates like a single organism, with each individual in a colony acting like a cell in the body and becomes a "super-organism." Federated deep learning algorithm requires these small players like insects, ants, critters and bees to create big and smart things with immense, complex and adaptive social power and ambitious missions.

In some embodiments, Flea end users communicate and collaborate with one another to build and update models of computation in vertical tensor ensembles in a one-to many manner. With federated learning a global protocol is sent from one central authority to many participants who collect information on their edge device, label the information and compute it locally, after which they sent the tensors to the central FL aggregator of the sponsor. They aggregate all the tensors and then report the updated and averaged tensors back to each of the participants.

Clinical Trials

Figure 3A:
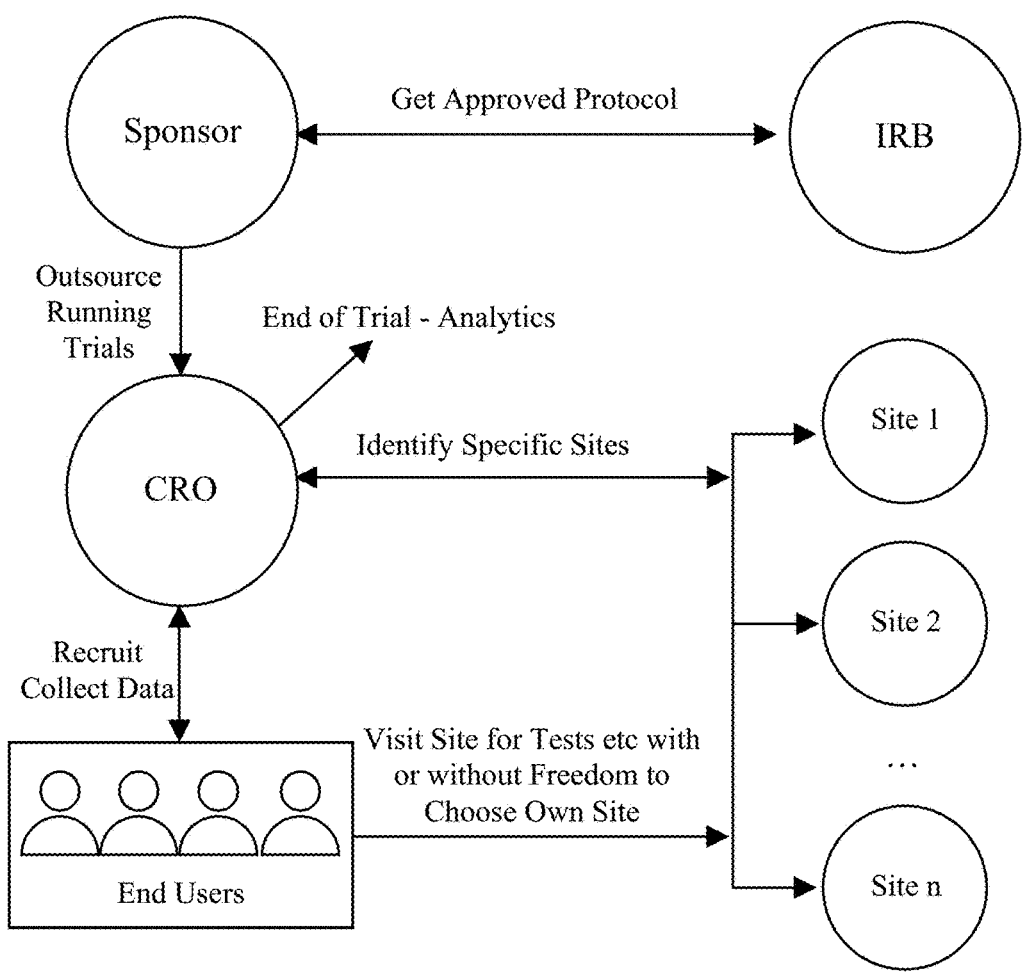
FIG. 3A is a diagram illustrating an example use case of a federated learner system, comprising one-to-many tensors for distributed clinical trials.

FIG. 3A is a diagram illustrating an example use case of a traditional clinical trial where the one-to-many tensors for distributed clinical trials could be applied.

In some embodiments, tensor ensembles are vertical in a one-to-many structure, called Vertical Tensor Ensembles. Most clinical trials are centralized which consist of one sponsor who centrally produces the protocol and uses several sites where many end users can go for physical exams and laboratory tests. This procedure is time consuming and costly and mostly outsourced to Contract Research Organizations (CROs). With Federated Learning a global protocol is sent from one central authority to many end users who collect information on their edge devices, e.g. smartphones, label the information and compute it locally, after which the outcome tensors are sent to the central FL aggregator of the sponsor. The central authority aggregates all the tensors and then reports the updated and averaged tensors back to each of the end users. This one-to-many tensors are configured to conduct distributed clinical trials.

Figure 3B:
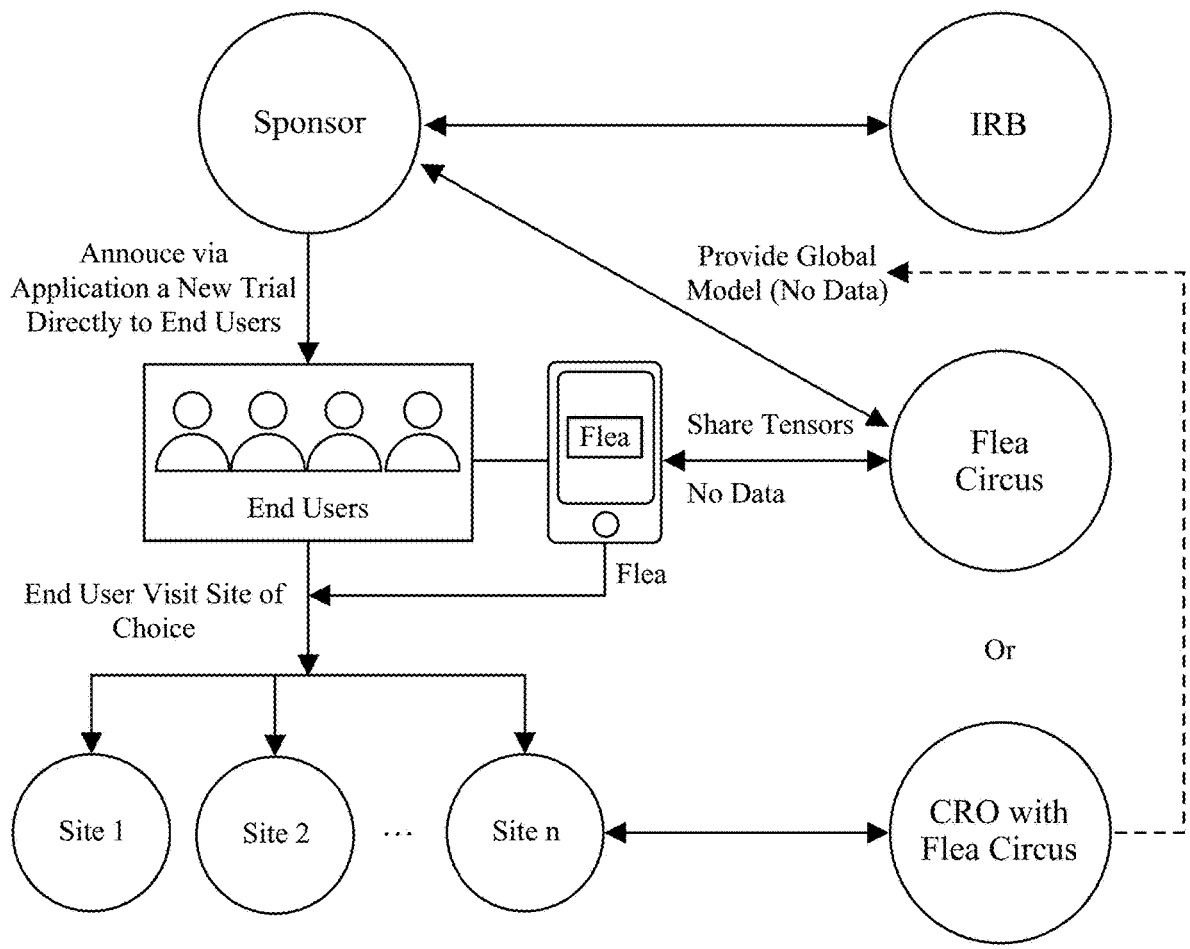
FIG. 3B is a diagram illustrating an example use case of a federated learner system, comprising Fleas for distributed clinical trials.

FIG. 3B is a diagram illustrating an example of using a federated learner system to conduct one-to-many tensor exchanges for distributed clinical trials, using so-called Fleas.

In some embodiments, sponsor of a digital clinical trial, typically a data trial, announces the data trial directly to end users via application program installed on end users' devices. Each end user device includes a federated learner. The federated learners are configured to share tensors with a centralized FL aggregator. The centralized FL aggregator is configured to share with the sponsor only a global model, not data or model updates from individual end users.

In some embodiments, sponsor of a data trial announces the trial directly to end users. End users are free to choose from many specific sites to participate the data trial. Each of these specific sites are configured to be connected with a CRO which holds FL aggregator. Similarly, federated learners of devices are configured to share tensors on data with the CRO FL aggregator. The CRO centralized FL aggregator is configured to share with the sponsor only a global model, not data or model updates from individual end users.

Both of these embodiments, comparing to traditional clinical trial procedure involving Institutional Review Board (IRB), improve the efficiency of clinical trials drastically. End users enjoy far better flexibility of participating clinical trials. The one-to-many trials reduce the need for a CRO from a data management perspective for Pharmaceutical company. End users are not sharing data, just trained models' weights. End users have the option to go to preferred site of choice, instead of being limited to a chosen and assigned site to them. This also means more virtual trials are possible without introducing data quality issues. The FL aggregator intermediary, either a centralized FL aggregator or a CRO having licensed FL aggregator, can do the global averaging of the weights. A sponsor, such as a pharmaceutical company, doesn't do the global averaging of the weights, thus removing doubts of any bias by the sponsor. The audits are on the weights and algorithms, thus removing most human bias in checking data quality.

Figure 4:
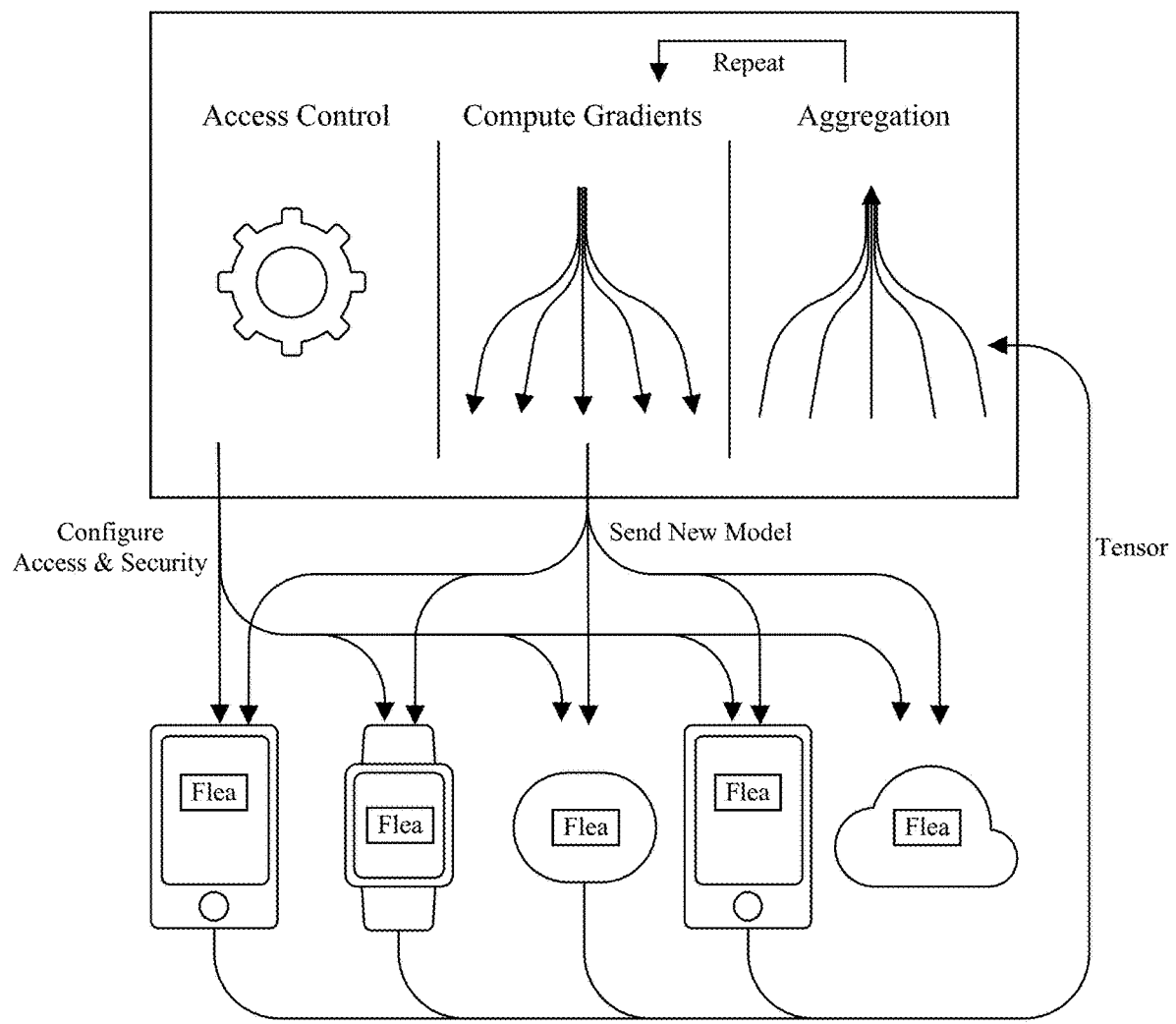
FIG. 4 is a diagram illustrating an example FL aggregator.

FIG. 4 is a diagram illustrating an example FL aggregator. In this example, Flea is configured to be embedded in various edge devices belonging to end users. Such edge devices can be but not limited to any electronic device which is capable of connecting to internet or similar web. For example, mobile phones, smart watches, sensor modules in car or home, or a cloud server, etc.

An FL aggregator is designed as a federated learning back-end responsible to collect model updates and evaluations sent from Flea end users which requires high availability, organize models that can be updated from end user side updates along with the operations required to perform these updates, admit or reject proposed updates from each end user based on criteria such as history of end user's submissions (e.g. an end user's credibility score) as well as end user sent metadata. The FL aggregator aggregates admissible end user updates into a single update to each model and redistributes updated models to the end user side. The FL aggregator reports aggregations of model evaluations based on similar admissibility criteria as those used in updates, It conducts tensorial handshakes, which are protocols that govern the exchange of information between federated learners running on end user devices and the FL aggregator, or amongst collectives of federated learners, on the initiative of end users themselves.

Figure 5:
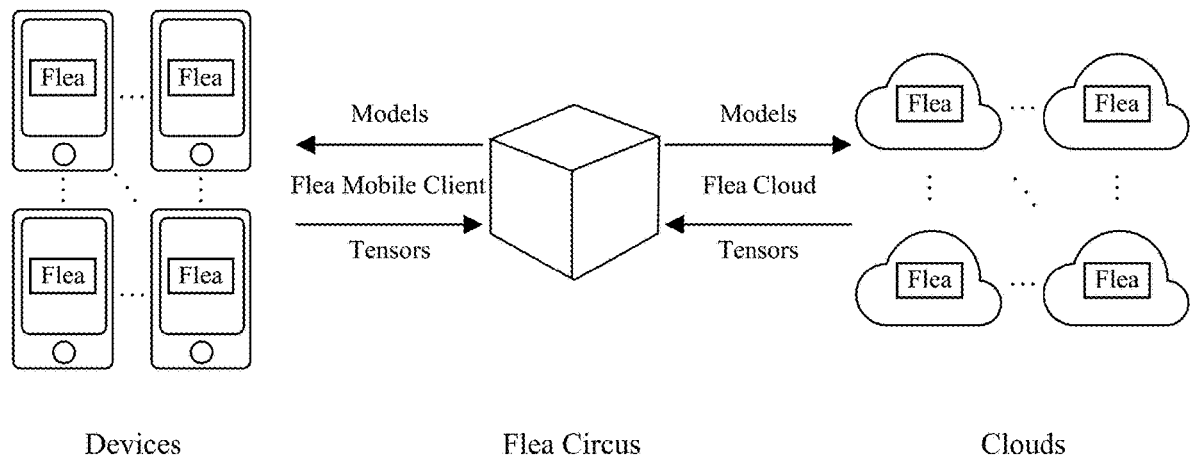
FIG. 5 is a diagram illustrating an example use case of tensor globalization of a federated learner system.

FIG. 5 is a diagram illustrating an example use case of tensor globalization of a federated learner system. Consider the example of a biotech company that has a federated learner model trained for Parkinson's disease. Traditionally, most clinical trials are centralized. They consist of one sponsor who centrally produces the protocol and uses several sites where the many participants can go for exams and tests. This procedure is time consuming and costly and mostly outsourced to Clinical Research Organizations (CROs).

New alternatives that are now becoming available as the technologies disclosed, which manipulate tensors as proxies for data, evolve. The distributed structure of a clinical trial, instead of flat, can be curved into an n-dimensional manifold or surface. This also changes the nature of models. Models themselves are simply tensor ensembles. As edge computational units become more powerful, each computational unit on the edge can house its own model.

Between edge units, both data-derived tensors and model ensembles can be freely exchanged.

The FL aggregator is configured to be provided at least a federated learner model and a multi-dimensional matrix. The tensors coming out of that model are to be averaged with the tensors of biotech model. The biotech company gets the global model back.

Another example use case applies the technology disclosed to an application program used by millions of members who regularly use the application for a function, leaving digital traces that reveal the members' interests in a data trail. For instance, someone may look for restaurants. In this example, the tech company requires user feedback in order to improve the quality of its prediction model to serve users better. The tech company gives this input to FL aggregator and gets the tensors back, asynchronously or synchronously. Doing so, the raw data of end users is not used, and privacy of end users is not invaded. The tech company only gets a global model of the interests of the entire population and a more precise model in different behavioral segments that enables them to target specific predicted actions. The company can also share either the global tensors or the precision tensors, should they want to. No data is transported, inferences can be drawn by applying the tensors, without access to underlying user data.

Figure 6A:
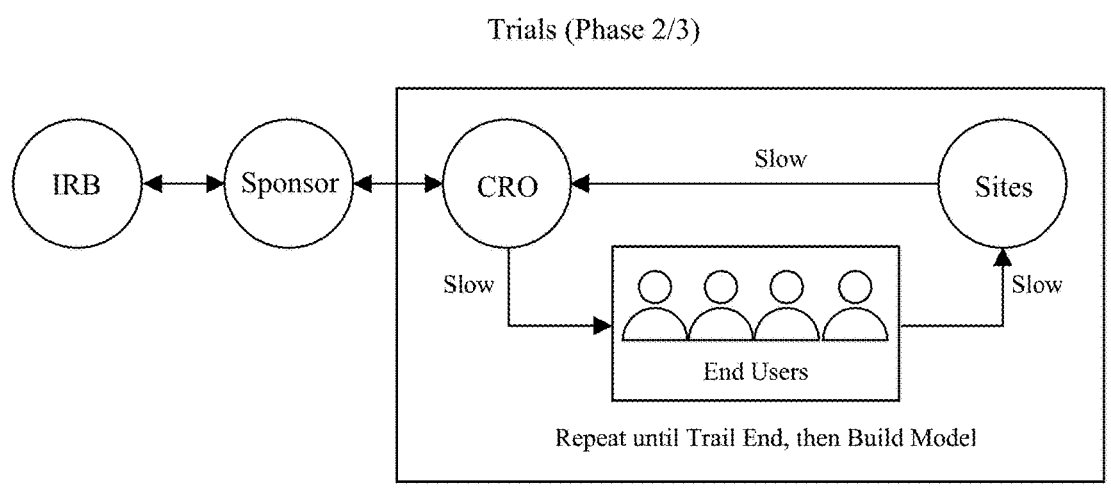
FIG. 6A and FIG. 6B are diagrams illustrating an example use case of a federated learner system in a linear training trial and in an adaptive and continuously learning distributed trial, comprising federated learners and FL aggregator for application of data trial.
Figure 6B:
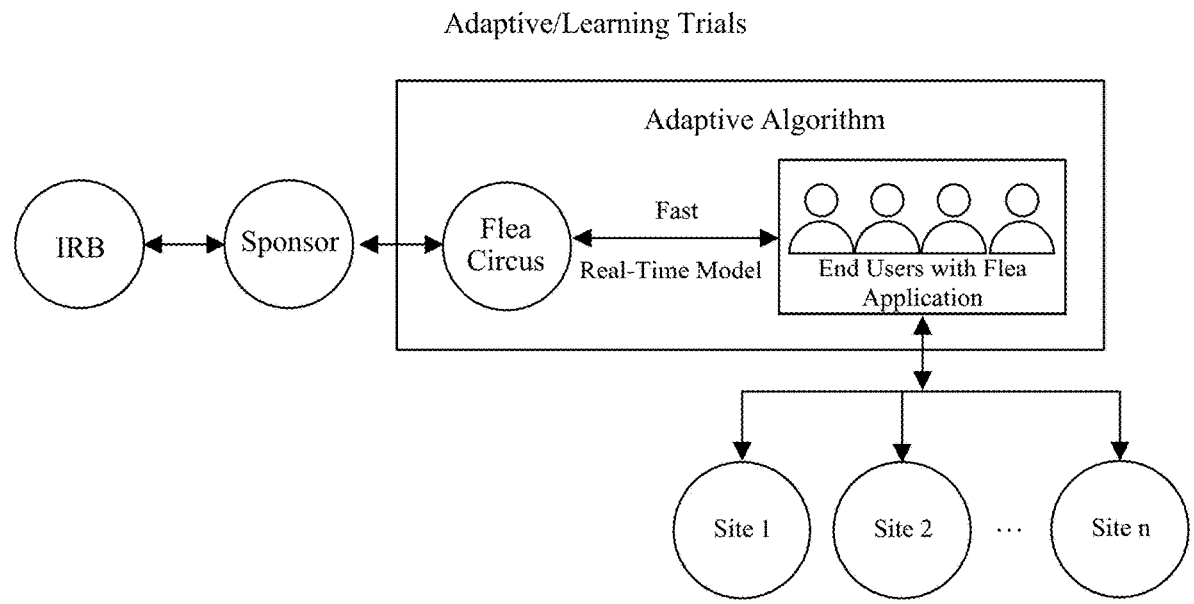

FIGS. 6A-6B are diagrams illustrating example use case of a federated learner system in a linear training trial and in an adaptive and continuously learning distributed trial, comprising federated learners and FL aggregator applied to collection and analysis of data trial.

With a federated learner and FL aggregator, clinical trials do not require site visits. On a site visit, CROs receive the data from the sites, which is an arduous data collection process that takes significant time. The CROs analyze the data once the trial is complete, which takes significant amount of time and money to do so. Correcting model errors is expensive, especially if a part of the trial has to be reevaluated. With federated learner, trials are in real-time, especially because end points of the trials are already being built as prediction models or analytics. Administrators can control the data training and frequency behind the scenes and it is the algorithms that are adaptive, instead of humans in a CRO. Trials are more streamlined and parallelized. Speed of trial is significantly improved, even though it may possibly mean failing fast. Feedback loops are much faster, and the sponsors or CROs get a much better idea whether the trial is even working correctly from early on.

An end user can use a site of their choice, provided the site is also chosen with the trial. The data on end user's phone is used for training the model relevant to the end point of the trial. Since the analytics and model are not an after-trial completion artifact but living and real-time with the federated learner, administrators of the trial can quickly adapt to issues of bias, confounding influences, etc. This speeds up trials. End users can be virtual or on-site. Additionally, trials can collect real world data from user devices that provides more dimensions for training.

Figure 7:
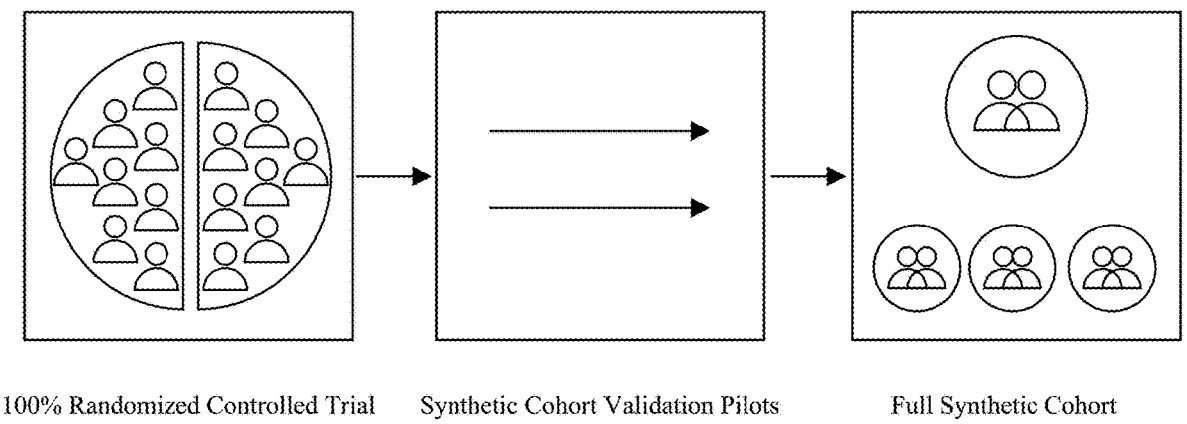
FIG. 7 is a diagram illustrating an example use case of a federated learner system, comprising simulated control arms for trials.

FIG. 7 is a diagram illustrating an example use case of a federated learner system, including one or more simulated control arms for the application of data trial. So-called synthetic control arms are configured to operate via collected data at large scale over an existing population. See, e.g., Goldsack, Syntehtic control arms can save time and money in clinical trials Feb. 5, 2019) <accessed at dub dub dub at statnews.com/2019/2/5/synthetic-control-arms-clinical-trials/>; Medidata, De-risk Go/No Go Product Development Decisions by Reusing Patient Trial Data: MEDS Synthetic Control Arms & Synthetic Control Data (2019) <accessed at dub dub dub dot medidata.com/en/white-paper/de-risk-go-no-go-product-development-decisions-by-reusing-patient-trial-data-meds-synthetic-control-arms-synthetic-control-data-2/>. The same populations can be used to train generative models for similar populations. These generative models can cause a many-fold increase in the utility of the population based on its simulated characteristics.

Instead of collecting data from patients recruited for a trial who have been assigned to the control or standard-of-care arm, synthetic control arms model those comparators using real-world data that has previously been collected from sources such as health data generated during routine care, including electronic health records, administrative claims data, patient-generated data from fitness trackers or home medical equipment, disease registries, and historical clinical trial data, etc. This can be done via a federated learning model with edge devices sending up gradients to at least one FL aggregator.

Synthetic control arms bring clear benefits to pharmaceutical industry and application. It can reduce or even eliminate to enroll control end users, improve efficiency, efficacy and consistency. By reducing or eliminating the need to enroll control end users, a synthetic control arm can increase efficiency, reduce delays, lower trial costs, and speed up life-saving therapies to market. This kind of hybrid trial design presents a less risky way for sponsors to introduce real-world data elements into regulatory trials and can also reduce the risk of late stage failures by informing go or no-go development decisions. Placebo-fear is one of the top-reasons patients choose not to participate in clinical trials. This concern is amplified when an individual's prognosis is poor and when current care is of limited effectiveness. Using a synthetic control arm instead of a standard control arm ensures that all participants receive the active treatment, eliminating concerns about treatment/placebo assignment. Use of a synthetic control arm addresses an important participant concerns and removes an important barrier to recruitment. The use of simulated control arms can also eliminate the risk of unblinding when patients lean on their disease support social networks posting details of their treatment, progress, and side effects that could harm the integrity of the trial.

The federated learner system can be utilized for tensorial twins. The tensorial twin represents the nearest-neighbor patient, derived from algorithmic matching of the maximal proportion of data points using a subtype of AI known as nearest-neighbor analysis. The nearest neighbor is identified using AI analytics for approximating a facsimile, another human being as close as possible to an exact copy according to the patient's characteristics to help inform best treatment, outcomes, and even prevention.

We can use information that comprehensively characterizes each individual for demographics, biologic omics, physiology, anatomy, and environment, along with treatment and outcomes for medical conditions.

Perturbed Subspace Method (PSM) employs a predicted probability of group membership, e.g., treatment or control group, based on observed predictors, usually obtained from logistic regression to create a counterfactual group. Propensity scores may also be used for matching or as covariates—alone or with other matching variables or covariates. With federated learning every cohort can be configured to be adaptive in a very complex way because the members with federated learner could send up delta. In this case, it continuously makes the relationship between them and the cohort tenuous to the point that they redefine normality and start to act as patients in silico, preparing for a stochastic forward model of precision medicine.

The federated learner system may use fuzzy tensor swarm. Devices which used to be responsible only for the gathering of data are to be configured to run downstream computations. Such configuration can be applied to various scenarios. For example, heart rate monitors, automatic blood pressure pumps, weather micro-stations, etc. Computational capacity as well as speed are increased drastically. With the advent of higher-bandwidth connectivity between such devices (due, for example, to 5G), the old paradigm of requiring these devices to send data to a central location where an archaic batch runner produces an updated data processor and ships it back to each device individually is becoming outmoded. Incurring a system-wide overhead when heart rate monitor can update its own data processing algorithms makes no sense any more. Such heart rate monitor system only requires access blood pressure pump and weather micro-station. As in the case of the heart rate monitor, the capability of updating the system's own data processing algorithm by the system itself is especially true for mission-critical functionality, where seconds could make a difference between life and death. To make use of this additional computational capacity and bandwidth, each device is to be deployed with its own adaptive data processing module, placed within a network mesh of devices, and equipped with an ontology (e.g., protocol-driven) describing to it the kind of information it can derive from each of its neighbors in the mesh. Each device in the mesh is configured to make available to its neighbors any of its primitives, as well as data-derived updates to itself. Taken together, an ensemble of interconnected devices, of which each with an intelligent data processing module and an ontological protocol, form a fuzzy tensor swarm. In this fuzzy tensor swarm, the emergent behavior is configured at a minimum equivalent in functionality, although may not be optimal in terms of latency and overhead, to what is possible with a centralized model building workflow. Empowered by 5G and Internet-of-Things technologies, each device can be connected, either physically or not, and stream data to millions of other smart data capture devices that can create live models of their vertical worlds. The enriched information from millions of graphics processing units can be feedbacked to other objects or their carbon, silicon or neuron users. Passive collection can be monetized and become the service industry of virtual reality (VR) which can create parallel existential dimensions as a service.

In some embodiments of the disclosure, a federated learner model can be applied to federated learning and adversarial rapid testing of clinical data and standards. Data training done on the device close to the data mitigates privacy concerns. The trained models basically try to predict when symptoms happen, and the user can be enabled to verify. This Generative Adversarial Models (GAN) can then be used to generate Real World Evidence (RWE) backed patient simulations to validate clinical trials, data, anomaly detection. Pharmaceutical company can be enabled to license these models out as new revenue. End users' simulated data is predicted or inferred on probabilistic risk calculators, based on their genetics, exposome, pharmacome and other omics data. Once these models are built, pharmaceutical company can also use the models in other data trials to do ground work analysis.

Clinical trial can go out with consumer health care mobile devices, e.g., apple watch, where participants can confirm or deny when the GAN thinks they may have a symptom happen soon. The model gets trained on end user devices and only the model is sent back to the servers. The models are then tested in other patients and verified over and over.

This model of symptoms can be used to simulate existing clinical trial around similar drug. If it can reproduce the study results, then these models can be used in dashboard around these types of drugs.

The federated learning model can be applied to automatic qualification of participants for clinical trials and remove the expensive human verification process.

The federated learning model can be applied to decentralized patient registries. Such registry is on the edge and fragmented, but comes together on an "ask" command by authorized personnel, e.g., the end user.

The federated learning model can be applied to configure peer to peer health data comparator to compare health condition of one end user against another without sharing any personal data.

The federated learning model can be applied to distribute second opinion. One end user can be enabled to share his or her personal model with a new doctor or citizen scientist without giving away any data. Tensors are compared and not the real data.

The federated learning model can be applied to health anomaly detection via model anomaly detection. Tensors can be configured to indicate that there is an out of bounds anomaly with the population. Once some issues identified, it can escalate to a doctor.

The federated learning model can be applied to health fingerprint. The model built on end user data can be a unique signature of the end user. It evolves as the health condition of the end user evolves. The model can be used as an identity in time.

Computer System

Figure 18:
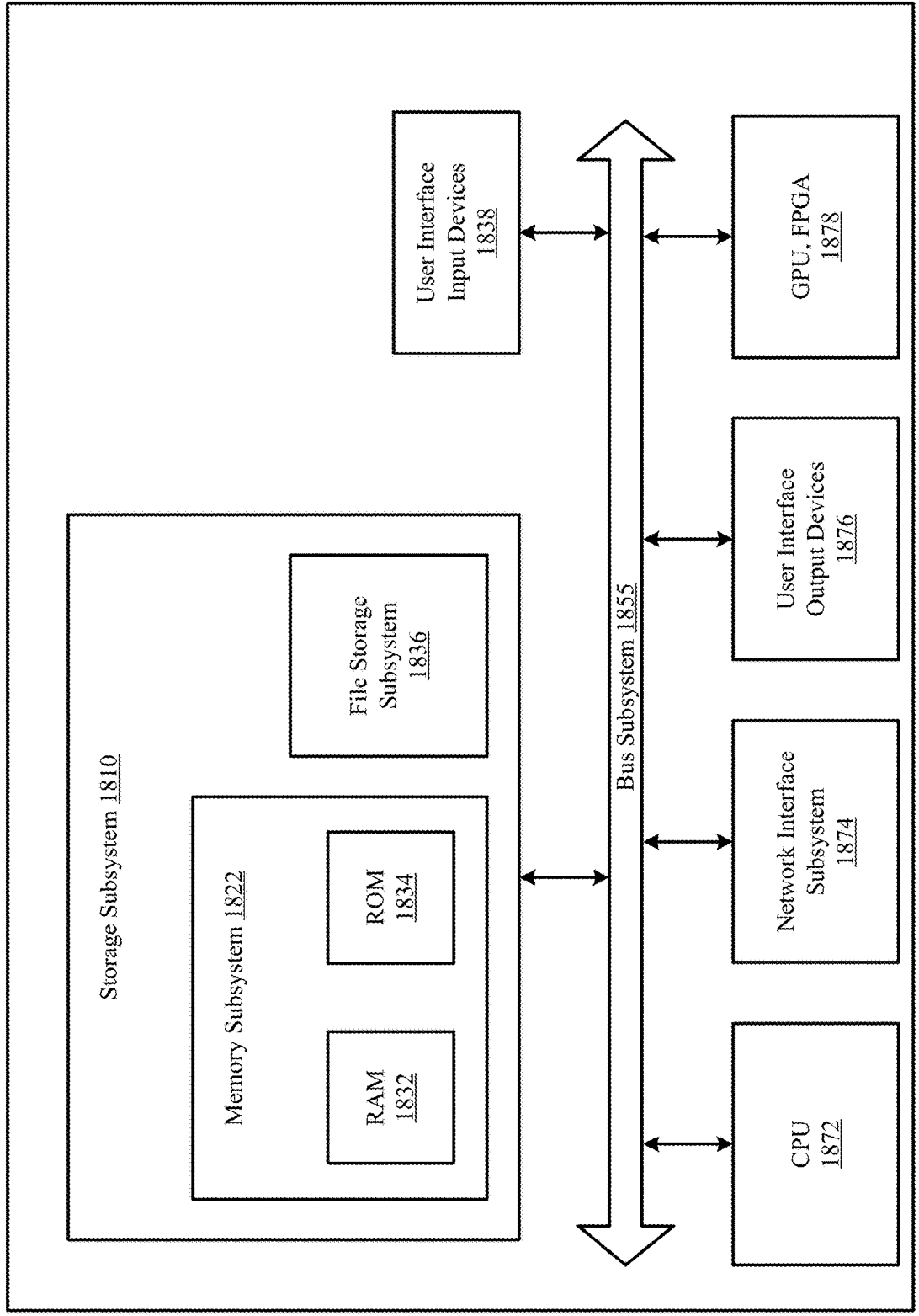
FIG. 18 is a simplified block diagram of a computer system that can be used to implement the technology disclosed.

FIG. 18 is a simplified block diagram of a computer system 1800 that can be used to implement the technology disclosed. Computer system typically includes at least one processor 1872 that communicates with a number of peripheral devices via bus subsystem 1855. These peripheral devices can include a storage subsystem 1810 including, for example, memory subsystem 1822 and a file storage subsystem 1836, user interface input devices 1838, user interface output devices 1876, and a network interface subsystem 1874. The input and output devices allow user interaction with computer system. Network interface subsystem provides an interface to outside networks, including an interface to corresponding interface devices in other computer systems.

User interface input devices 1838 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices 1876 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem 1810 stores programming and data constructs that provide the functionality of some or all of the modules and methods described herein. These software modules are generally executed by processor alone or in combination with other processors.

Memory used in the storage subsystem can include a number of memories including a main random access memory (RAM) 1832 for storage of instructions and data during program execution and a read only memory (ROM) 1834 in which fixed instructions are stored. The file storage subsystem 1836 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem 1855 provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 18 is intended only as a specific example for purposes of illustrating the technology disclosed. Many other configurations of computer system are possible having more or less components than the computer system depicted in FIG. 18.

The computer system 1800 includes GPUs or FPGAs 1878. It can also include machine learning processors hosted by machine learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

Some Particular Implementations

We disclose use of federated learning in a variety of heathcare applications that typically involve sensitive, private data.

One disclosed implementation includes a system for federated learning. The system includes multiple edge devices of end users, coupled to a communication network. The edge devices include a memory that stores program instructions for a federated learner, recorded user data, and a tensor of model parameters of a deep neural network, a "DNN". The federated learner executes on a processor of the edge device. The federated learner is configured to record end user data, predict characteristics of the end user from the recorded end user data by applying the DNN, and receive updates from the end user that correct the predicted end user characteristics. The federated learner is further configured to perform update training of the DNN using the recorded user data and the corrected user characteristics, thereby producing a modified tensor of updated model parameters and send at least a modified part of the modified tensor to an FL aggregator.

The system further includes a base model tensor of model parameters for the DNN running on the edge devices, trained to predict characteristics of the end users from the recorded end user data, provided to the edge devices.

The FL aggregator is coupled to a communication network and includes a federated learner. The federated learner is configured to receive modified tensors from at least some of the edge devices, aggregate the modified tensors with a current version of the base model tensor by federated learning to produce a new version of the base model tensor, and distribute the new version of the base model tensor to the edge devices. The federator learner can be implemented in the FL aggregator as in-line code, can be implemented in a separate module or some combination of the two coding strategies.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The recorded end user data can include a picture captured by the edge device, an audio recording of the end user captured by the edge device, or both. When the recorded end user data includes a frontal face picture captured by the edge device, the predicted end user characteristics include age, height and weight. Sex also can be predicted and BMI calculated from a combination of predicted features. When the recorded end user data includes an audio recording of the end user captured by the edge device, with or without a face image, the predicted end user characteristics can include mood.

On the edge device, a face detector can be applied to determines whether a face appears in the picture, limit update training of a facial interpretation model, avoiding, for instance, training on cat or sunset pictures.

On the FL aggregator side, the federated learner can be configured to filter out spurious updates by calculating a distance measure that compares each modified tensor received from the edge devices to the base model tensor, constructing a distribution of distance measures in an updating cycle and rejecting from aggregation with the current version of outlier modified tensors. That is, production of the new base model version, will not be based on rejected tensors having a distance measure that are outliers from the distribution. An outlier can be determined using a statistical measure such as three standard deviations or the like.

Other implementations may include a non-transitory computer readable storage medium storing instructions executable by a processor to perform actions of the system described above. Each of the features discussed in the particular implementation section for other implementations apply equally to this implementation. As indicated above, all the other features are not repeated here and should be considered repeated by reference.

In other implementations, the technology disclosed presents methods of operating the edge devices, the server or FL aggregator device, or both.

One method implementation disclosed involves federated learning utilizing computation capability of edge devices. The edge devices used to practice this method include a memory, storing store program instructions for a federated learner, recorded user data and a tensor of model parameters of a deep neural network, a "DNN". The federated learner executes on a processor of the edge device, and is configured to: record end user data; predict characteristics of the end user from the recorded end user data by applying the DNN; receive updates from the end user that correct the predicted end user characteristics, and perform update training of the DNN using the recorded user data and the corrected user characteristics.

This method implementation includes sending a current base model tensor of the model parameters to the edge devices and receiving modified tensors from at least some of the edge devices, based on at least user data recorded by the edge devices and corrected user characteristics received by the edge devices from end users. It can involve checking to determine that the modified tensors received apply to the current version of the base model tensor, not to a prior, outdated version. Because updating is an asynchronous process and user behavior is not under the system's control, it is expected that some users will not participate in a cycle, some edge devices will not receive the current version of the base model tensor, and some edge devices will offer updates to an expired or outdated version of the base model tensor.

This method further includes aggregating the modified tensors with a current version of the base model tensor by federated learning to produce a new version of the base model tensor and distributing the new version of the base model tensor to the edge devices. The receiving, aggregating and distributing actions are repeated for at least ten cycles. These actions may be repeated 50 or 100 or 1000 times or more. The cycles of the FL aggregator and its components will repeat more times than most users participate in collecting data and retraining base models.

Features described above for the system and described through out the application for systems and methods can be combined with this method, cast as it is from the server's perspective. In the interest of conciseness, not every combination of features is enumerated.

When the recorded end user data includes a frontal face picture captured by the edge device, the and the predicted end user can include characteristics include age, height and weight. The method can further include constructing an initial current version of the base model from a generic face recognition model, with additional layers added and training applied with ground truth for the age, height and weight of persons in at least some frontal face pictures. This initial current version is prepared before the edge devices make available any recorded images or corrected user characteristics.

When the recorded end user data includes an audio recording of the end user captured by the edge device, the method can include predicting the end user's mood.

The method can further include filtering before aggregating, such as by calculating a distance measure that compares each modified tensor received from the edge devices to the base model tensor and constructing a distribution of distance measures in an updating cycle. As described in more detail above, this distribution can be used to reject at least one modified tensor from aggregation, as an outlier from the distribution.

Another method implementation of the technology disclosed is presented from the perspective of an edge device contributing to federated learning. The edge device cooperates with an FL aggregator that is configured to receive modified tensors from a plurality of edge devices, aggregate the modified tensors with a current version of a base model tensor by federated learning to produce a new version of the base model tensor, and distribute the new version of the base model tensor to the edge devices.

This method includes the edge device receiving a version of the base model, including a tensor of model parameters of a deep neural network, a "DNN" and recording end user data. The method includes predicting characteristics of the end user from the recorded end user data by applying the DNN and causing display of the predicted characteristics to the end user. Responsive to the display, the method includes receiving updates from the end user that correct the predicted end user characteristics. The edge device performs update training of the DNN on the edge device, using the recorded user data and the corrected user characteristics, to produce a modified tensor of updated model parameters. The method further includes sending at least a modified part of the modified tensor to an FL aggregator and receiving new version of the base model tensor from the FL aggregator, after the FL aggregator aggregated modified tensors from a plurality of edge devices with the base model by federated learning. The recording, predicting, receiving updates, performing, and sending actions are repeated by the edge device in at least five cycles. The actions can be repeated in at least 10 or 50 cycles or even 100 cycles. An edge device, such as a mobile phone carried by an end user, is unlikely to participate in all of the cycles managed by the FL aggregator, unless data is being relayed automatically to and processed by the edge device, or an app collects data from the user on a daily basis. Examples of personal devices that are capable of automatically relaying data to a personal device include a blood glucose monitor, a pace maker, a heart rate monitor, an exercise monitor, a fall monitor, a pulse oximeter, a scale (with or without body fat estimation), and a breathing assistance device. Use of such devices can result in more frequent participation by the edge device in training cycles, even in 1,000 cycles or more. Examples of applications that collect data from the user on a daily basis include diet or consumption logging applications, exercise applications and meditation applications.

Features described above for the system and described through out the application for systems and methods can be combined with this method, cast as it is from the edge device's perspective. In the interest of conciseness, not every combination of features is enumerated.

When the recorded end user data includes a frontal face picture captured by the edge device, the predicted end user characteristics can include age, height and weight. When the recorded end user data includes an audio recording of the end user, with our without a face image, the predicted end user characteristics can include mood.

The method can further include filtering of images before using the images for update training. A face detector can be applied to determine whether a face appears in the picture, before performing update training using the picture. This can prevent training against pictures of kittens and sunsets, when the system is designed to interpret human faces.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One disclosed implementation may include a tangible non-volatile computer readable storage media loaded with computer program instructions that, when executed on a server, cause a computer to implement any of the methods described earlier.

Another disclosed implementation may include a server system including one or more processors and memory coupled to the processors, the memory loaded with instructions that, when executed on the processors, cause the server system to perform any of the methods described earlier.

This system implementation and other systems disclosed optionally can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

While the technology disclosed is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the innovation and the scope of the following claims.

We claim as follows:
1. A system for federated learning, comprising:
multiple edge devices of end users, coupled to a communication network, each edge device comprising
  a memory, that stores program instructions for a federated learner, recorded user data, and a tensor of model parameters of a deep neural network, a "DNN"; and
  the federated learner, that executes on a processor of the edge device, configured to:
    record end user data,
    predict characteristics of the end user from the recorded end user data by applying the DNN,
    receive updates from the end user that correct the predicted end user characteristics,
    perform update training of the DNN using the recorded end user data and the corrected user characteristics, thereby producing a modified tensor of updated model parameters, and send at least a modified part of the modified tensor to an FL aggregator;

a base model tensor of model parameters for the DNN running on the edge devices, trained to predict characteristics of the end users from the recorded end user data, provided to the edge devices;

the FL aggregator, coupled to a communication network, comprising a federated learner,
configured to
receive modified tensors from at least some of the edge devices,
aggregate the modified tensors with a current version of the base model tensor by federated learning to produce a new version of the base model tensor, and
distribute the new version of the base model tensor to the edge devices, and wherein the recorded end user data includes a picture captured by the edge device, each edge device further comprising a face detector that determines whether a face appears in the picture and proceeds to perform update training only upon detection of a face in the picture.

2. The system of claim 1, wherein the recorded end user data includes an audio recording of the end user captured by the edge device.

3. A non-transitory computer readable media including program instructions that, when loaded into the memory of the multiple edge devices of end users, and loaded into memory of the LF aggregator or its components, produces a system according to claim 2.

4. The non-transitory computer readable media of claim 3, wherein the predicted end user characteristics include mood.

5. The system of claim 1, wherein the recorded end user data includes a frontal face picture captured by the edge device and the predicted end user characteristics include age, height and weight.

6. A non-transitory computer readable media including program instructions that, when loaded into the memory of the multiple edge devices of end users, and loaded into memory of the LF aggregator or its components, produces a system according to claim 5.

7. The system of claim 1, wherein the recorded end user data includes an audio recording of the end user captured by the edge device and the predicted end user characteristics include mood.

8. The system of claim 1, wherein the recorded end user data includes a frontal face picture and an audio recording of the end user captured by the edge device and the predicted end user characteristics include mood.

9. The system of claim 1, the federated learner further configured to:
calculate a distance measure that compares each modified tensor received from the edge devices to the base model tensor;
construct a distribution of distance measures in an updating cycle; and
reject at least one modified tensor from aggregation with the current version of the base model tensor to produce the new version, based on the rejected tensor having a distance measure that is an outlier from the distribution.

10. A non-transitory computer readable media including program instructions that, when loaded into the memory of the multiple edge devices of end users, and loaded into memory of the LF aggregator or its components, produces a system according to claim 9.

11. A non-transitory computer readable media including program instructions that, when loaded into the memory of the multiple edge devices of end users, and loaded into memory of the LF aggregator or its components, produces a system according to claim 1.

12. The system of claim 1, wherein the recorded end user data includes a frontal face picture captured by the edge device.

13. The system of claim 1, wherein the predicted end user characteristics include at least one of age, height, and weight.

14. A method of contributing to federated learning, FL, applied by an FL aggregator utilizing computation capability of an edge device, wherein the FL aggregator is configured to:
receive modified tensors from a plurality of edge devices,
aggregate the modified tensors with a current version of a base model tensor by federated learning to produce a new version of the base model tensor, and
distribute the new version of the base model tensor to the edge devices;

the method comprising the edge device:
receiving a version of the base model, including a tensor of model parameters of a deep neural network, a "DNN";
recording end user data;
predicting characteristics of the end user from the recorded end user data by applying the DNN and causing display of the predicted characteristics to the end user;
receiving updates from the end user that correct the predicted end user characteristics;
performing update training of the DNN on the edge device using the recorded end user data and the corrected user characteristics, thereby producing a modified tensor of updated model parameters;
sending at least a modified part of the modified tensor to the FL aggregator;
receiving the new version of the base model tensor from the FL aggregator, after the FL aggregator aggregated modified tensors from the plurality of edge devices with the base model by federated learning; and
repeating the recording, predicting, receiving updates, performing, and sending actions in at least five cycles; and wherein the recorded end user data includes a picture captured by the edge device, each edge device further comprising a face detector that determines whether a face appears in the picture and proceeds to perform update training only upon detection of a face in the picture.

15. The method of claim 14, wherein the recorded end user data includes a frontal face picture captured by the edge device and the predicted end user characteristics include age, height, and weight.

16. The method of claim 14, wherein the recorded end user data includes an audio recording of the end user captured by the edge device and the predicted end user characteristics include mood.

17. The method of claim 14, wherein the recorded end user data includes a frontal face picture and an audio recording of the end user captured by the edge device and the predicted end user characteristics include mood.

18. The method of claim 14, wherein the recorded end user data includes an audio recording of the end user captured by the edge device.

19. The method of claim 14, wherein the FL aggregator is further configured to:
- calculate a distance measure that compares each modified tensor received from the edge devices to the base model tensor;
- construct a distribution of distance measures in an updating cycle; and
- reject at least one modified tensor from aggregation with the current version of the base model tensor to produce the new version, based on the rejected tensor having a distance measure that is an outlier from the distribution.

20. The method of claim 14, wherein the predicted end user characteristics include at least one of age, height, and weight.

* * * * *